US009660409B2

(12) United States Patent
Chuang

(10) Patent No.: US 9,660,409 B2
(45) Date of Patent: *May 23, 2017

(54) LOW NOISE, HIGH STABILITY, DEEP ULTRA-VIOLET, CONTINUOUS WAVE LASER

(71) Applicant: KLA-Tencor Corporation, Milpitas, CA (US)

(72) Inventor: Yung-Ho Chuang, Cupertino, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/017,839

(22) Filed: Feb. 8, 2016

(65) Prior Publication Data
US 2016/0197449 A1 Jul. 7, 2016

Related U.S. Application Data

(63) Continuation of application No. 14/080,746, filed on Nov. 14, 2013, now Pat. No. 9,293,882.
(Continued)

(51) Int. Cl.
H01S 3/00 (2006.01)
G02F 1/37 (2006.01)
(Continued)

(52) U.S. Cl.
CPC ....... *H01S 3/0092* (2013.01); *G01N 21/9501* (2013.01); *G02F 1/37* (2013.01);
(Continued)

(58) Field of Classification Search
CPC . H01S 3/0092; H01S 3/0085; G01N 21/9501; G01N 2201/067;
(Continued)

(56) References Cited

U.S. PATENT DOCUMENTS 2,672,072 A * 3/1954 Sachtleben ............ G03B 33/12
348/237
5,339,324 A 8/1994 Eguchi et al.
(Continued)

FOREIGN PATENT DOCUMENTS

DE 102005015497 A1 10/2006
WO 02/44807 A3 6/2002
(Continued)

OTHER PUBLICATIONS

Black, E. "Notes on the Pound-Drever-Hall technique", LIGO Technical Note LIGO-T980045-00-D, Caltech and MIT, Apr. 16, 1998, 15 pgs., http://www.ligo.caltech.edu/docs/T/T980045-00.pdf.
(Continued)

*Primary Examiner* — Xinning Niu
(74) *Attorney, Agent, or Firm* — Bever, Hoffman & Harms, LLP

(57) ABSTRACT

A laser for generating deep ultra-violet (DUV) continuous wave (CW) light includes a second-harmonic generator and a fourth-harmonic generator. The fourth-harmonic generator includes a plurality of mirrors as well as a first non-linear optical (NLO) crystal and a pair of tilted plates. The first NLO crystal generates the light having the fourth harmonic wavelength and a first astigmatism, and is placed in operative relation to the plurality of mirrors. The pair of tilted plates is placed in operative relation to the first NLO crystal such that the light having the second harmonic wavelength passes through both of the tilted plates. Notably, the pair of tilted plates are disposed at substantially equal and opposite angles about respective parallel axes such that they introduce a second astigmatism that corrects for the first astigmatism while minimizing displacement of the circulated light.

11 Claims, 11 Drawing Sheets

Related U.S. Application Data

(60) Provisional application No. 61/876,201, filed on Sep. 10, 2013.

(51) Int. Cl.
| | | |
|---|---|---|
| *G01N 21/95* | (2006.01) | |
| *G02F 1/35* | (2006.01) | |
| *G01N 21/33* | (2006.01) | |
| *G01N 21/956* | (2006.01) | |

(52) U.S. Cl.
CPC ............ *H01S 3/0085* (2013.01); *G01N 21/33* (2013.01); *G01N 2021/95676* (2013.01); *G01N 2201/067* (2013.01); *G02F 1/35* (2013.01); *G02F 2201/16* (2013.01)

(58) Field of Classification Search
CPC  G01N 2021/95676; G01N 21/33; G02F 1/37; G02F 2201/16; G02F 1/35
See application file for complete search history.

(56) References Cited

U.S. PATENT DOCUMENTS

| | | | |
|---|---|---|---|
| 5,367,531 A | 11/1994 | Eguchi et al. | |
| 5,418,810 A | 5/1995 | Eguchi et al. | |
| 5,563,702 A | 10/1996 | Emery et al. | |
| 5,625,633 A | 4/1997 | Ichimura et al. | |
| 5,936,761 A | 8/1999 | Kubota et al. | |
| 5,943,353 A * | 8/1999 | Kaneko .................. | H01S 3/109 372/22 |
| 5,999,310 A | 12/1999 | Shafer et al. | |
| 6,018,413 A | 1/2000 | Oka | |
| 6,181,461 B1 | 1/2001 | Wada et al. | |
| 6,201,601 B1 | 3/2001 | Vaez-Iravani et al. | |
| 6,271,916 B1 | 8/2001 | Marxer et al. | |
| 6,285,691 B1 * | 9/2001 | Kaneda ................ | H01S 3/2383 372/18 |
| 6,633,594 B1 | 10/2003 | Kiriyama et al. | |
| 6,862,131 B2 | 3/2005 | Masuda | |
| 7,027,209 B2 | 4/2006 | Zanger et al. | |
| 7,352,457 B2 | 4/2008 | Kvamme et al. | |
| 7,525,649 B1 | 4/2009 | Leong et al. | |
| 7,528,943 B2 | 5/2009 | Brown et al. | |
| 7,773,643 B2 | 8/2010 | Masuda | |
| 7,920,607 B2 | 4/2011 | Furutachi et al. | |
| 8,422,119 B1 * | 4/2013 | Keaton ..................... | G02F 1/35 359/326 |
| 8,432,944 B2 * | 4/2013 | Romanovsky ..... | G02B 27/0068 359/831 |
| 2006/0176916 A1 | 8/2006 | Zanger et al. | |
| 2007/0002465 A1 | 1/2007 | Chuang et al. | |
| 2009/0180176 A1 | 7/2009 | Armstrong et al. | |
| 2011/0220815 A1 | 9/2011 | Sakuma et al. | |
| 2011/0228263 A1 | 9/2011 | Chuang et al. | |
| 2013/0021602 A1 | 1/2013 | Dribinski et al. | |
| 2013/0077086 A1 | 3/2013 | Chuang et al. | |
| 2013/0088706 A1 | 4/2013 | Chuang et al. | |
| 2013/0135711 A1 | 5/2013 | Alekel et al. | |

FOREIGN PATENT DOCUMENTS

| | | |
|---|---|---|
| WO | 02/48785 A2 | 6/2002 |
| WO | 2004/066460 A1 | 8/2004 |
| WO | 2010/037106 A2 | 4/2010 |

OTHER PUBLICATIONS

Drever, R.W.P. et al., "Laser Phase and Frequency Stabilization Using an Optical Resonator", Applied Physics B, vol. 31, No. 2, Jun. 1983, pp. 97-105.

Hansch, T. W. and B. Couillaud: "Laser Frequency Stabilization by Polarization Spectroscopy of a Reflecting Reference Cavity", Optics Communications, vol. 35, No. 3, Dec. 1980, pp. 441-444.

\* cited by examiner

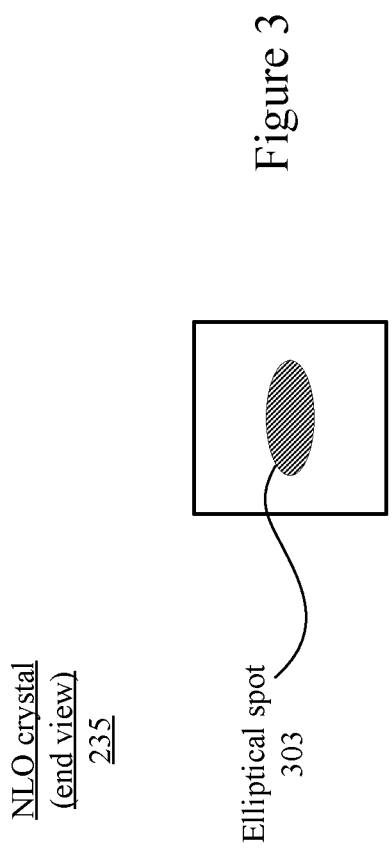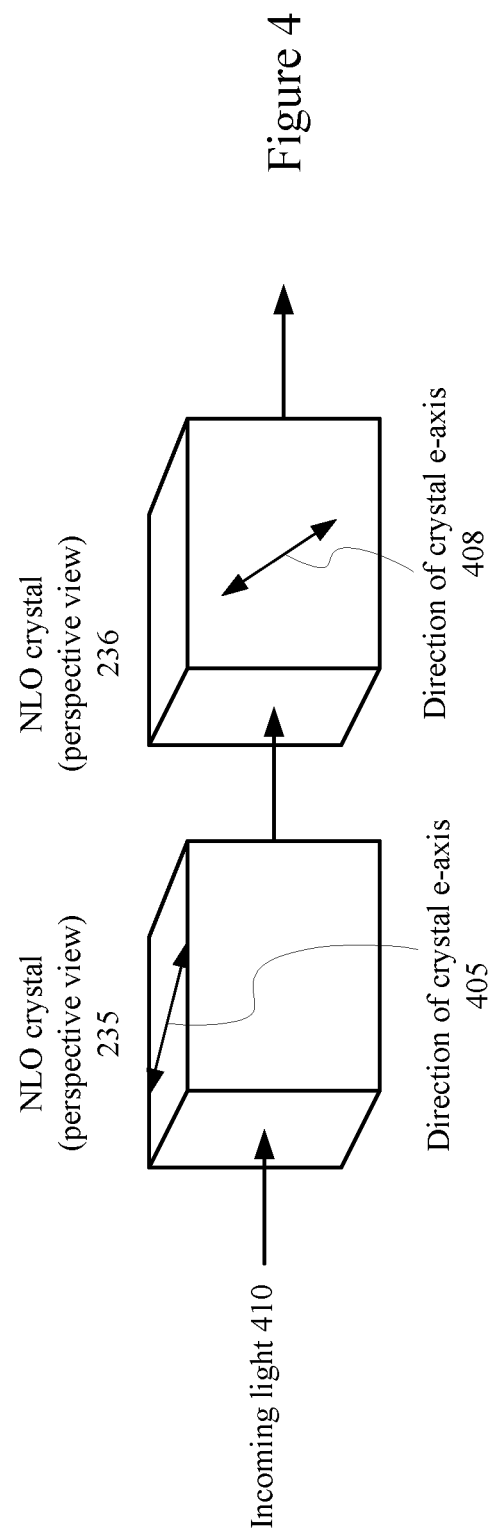

C
LOW NOISE, HIGH STABILITY, DEEP ULTRA-VIOLET, CONTINUOUS WAVE LASER

PRIORITY APPLICATION

This application is a continuation of U.S. patent application Ser. No. 14/080,746 entitled "LOW NOISE, HIGH STABILITY, DEEP ULTRA-VIOLET, CONTINUOUS WAVE LASER" filed Nov. 14, 2013 which claims priority of U.S. Provisional Patent Application 61/876,201, entitled "CW DUV Laser With Improved Stability" filed Sep. 10, 2013, and incorporated by reference herein.

BACKGROUND OF THE INVENTION

Field of the Invention

The present invention relates to low-noise, high-stability, deep ultra-violet (DUV), continuous wave (CW) lasers as well as inspection and metrology systems including such lasers.

Related Art

Semiconductor inspection and metrology require very stable, low-noise light sources to detect small defects and/or make very precise measurements of small dimensions. UV light sources are important because, in general, shorter wavelengths give better sensitivity to small defects or dimensions.

Low-noise, high-stability lasers are currently available for wavelengths in the visible and near infra-red (IR). However, there are very few CW lasers available for wavelengths in the DUV. Even when available, such lasers are expensive and noisy, have poor long-term stability, and may require frequent adjustments and/or service. Moreover, such lasers typically have powers less than 250 mW, whereas higher powers are desirable for most industry applications because they enable faster and more precise inspection and measurement.

Known DUV CW lasers typically operate by generating a fourth harmonic of an IR fundamental laser. Two frequency conversion stages are typically used, wherein a first stage generates a second harmonic frequency (also called a second harmonic) from a fundamental frequency and a second stage generates a fourth harmonic frequency (also called the fourth harmonic) using the second harmonic frequency. Each frequency-doubling stage (i.e. the first and second stages) uses a non-linear optical (NLO) crystal.

The frequency-doubling process depends on the square of the electric field strength, which is known by those skilled in the art. Therefore, if the power density inside the NLO crystal is low, then the conversion process is very inefficient. An IR laser of a few Watts or even a few tens of Watts of power, when focused into a NLO crystal, produces very little second harmonic because of its low power density. In contrast, a pulsed laser can provide a peak power density many times higher than its average power density. As a result, a pulsed laser of similar time-averaged power density to that of the IR laser can produce substantial amounts of the second harmonic. For example, in some pulsed lasers, roughly 50% of the input of a pulsed laser can be converted to the second harmonic.

A DUV CW laser can use a resonant cavity (also called a cavity) to increase the power density in its NLO crystal, thereby improving its conversion efficiency. Most of the light that passes through the NLO crystal without being converted to the second harmonic is re-circulated in the cavity to build up the power density. Any second harmonic that is produced is allowed to pass out of the cavity. Eventually, the power density builds up to a level where the power leaving the cavity as the second harmonic plus the losses in the cavity equals the input power and so a steady state is reached. To generate the DUV wavelengths, typically two resonant cavities can be connected in series. The first cavity generates the second harmonic (e.g. a visible wavelength, such as 532 nm) by recirculating the IR fundamental wavelength. The second cavity, which is serially coupled to the first cavity, generates the fourth harmonic (e.g. a DUV wavelength, such as 266 nm) by recirculating the second harmonic. Note that the term "coupled" as used to describe the cavities and/or components of the cavities may or may not include components of the cavities physically touching.

FIG. 1 illustrates an exemplary known laser configuration using two cavities, wherein a first cavity implements a second harmonic generator 102A and a second cavity implements a fourth harmonic generator 102B. The second harmonic generator 102A includes a plurality of mirrors 110, 111, 112, and 113 and a NLO crystal 115 to generate the second harmonic. The fourth harmonic generator 102B includes a plurality of mirrors 130, 131, 132, and 133 and a NLO crystal 135 to generate the fourth harmonic. The second harmonic generator 102A can be actively controlled using an oscillator 104 (generating a signal at frequency f1), a modulator 103, a photodiode 105, and a synchronous detector 106. Similarly, the fourth harmonic generator 102B can be actively controlled using an oscillator 124 (generating a signal at frequency f2), a modulator 123, a photodiode 125, and a synchronous detector 126.

IR light (e.g. at 1064 nm) from a fundamental laser 101 enters the second harmonic generator 102A through mirror 110 and, after reflecting from mirrors 111 and 112, enters NLO crystal 115. A portion of the IR light entering NLO crystal 115 is converted to the second harmonic (e.g. to 532 nm). Mirror 113 is coated with a material that reflects the IR light, but transmits the second harmonic. As a result, the second harmonic light passes through mirror 113 and is directed to the fourth harmonic generator 102B.

Most of the IR light passing through crystal 115 emerges from NLO crystal 115 without being converted and thus is reflected by mirror 113 and directed back to mirror 110. Mirror 110 is coated with a material that is highly reflective to the IR light arriving at the angle of incidence of the ray from mirror 113, but is highly transmissive to the incoming IR light from fundamental laser 101.

To build up a high power density in the second harmonic generator 102A, the IR light that has circulated in the first cavity should arrive at mirror 110 in phase with the incoming light from fundamental laser 101. To this end, a servo control can be used to mechanically move mirror 111 to achieve a predetermined cavity length, thereby providing the desired phase. In the configuration shown in FIG. 1, the servo control for the second harmonic generator 102A includes oscillator 104, modulator 103, photodiode 105, synchronous detector 106, and an actuator control 107. Similarly, the servo control for the fourth harmonic generator 102B includes oscillator 124, modulator 123, photodiode 125, synchronous detector 126, and an actuator control 127. An exemplary actuator control can include a piezo-electric transducer or a voice coil to maintain the predetermined cavity length and thus maximize the power density in the cavity.

As shown in FIG. 1, the input IR light from fundamental laser 101 is modulated by modulator 103 at frequency f1 (provided by oscillator 104) to provide a time-varying signal. Note that the coating on any mirror is imperfect, thereby allowing some leakage. As a result, photodiode 105 receives a small portion of the light circulating in the first cavity (i.e. that light reflected by mirror 113 via mirror 110) to provide a signal to synchronous detector 106. Synchronous detector 106 (which could include a mixer or some other similar component) compares the output of photodiode 105 with the output of oscillator 104 at frequency f1 to generate a control signal for actuator control 107. Specifically, synchronous detector 106 can determine whether the length of the first cavity needs to be adjusted and, if so, whether the length should be increased or decreased and by how much. Exemplary servo controls are described in U.S. Pat. No. 5,367,531, as well as in LIGO Technical Note LIGO-T980045-00-D by Black (1998).

A second modulator 123 modulates the input light to the fourth harmonic generator 102B (provided by mirror 113) at frequency f2 to provide another time-varying signal. Photodiode 125 detects a small portion of the circulating light (from mirror 133 via mirror 130). Synchronous detector 106 compares the output of photodiode 125 with the output of oscillator 124 at frequency f2 to generate a control signal for actuator control 127. Specifically, synchronous detector 126 can determine whether the length of the fourth harmonic generator 102B needs to be adjusted and, if so, whether the length should be increased or decreased. Actuator control 127 physically controls the position of mirror 131 to maintain the appropriate length of the fourth harmonic generator 102B so that the phase of the reflected light from mirror 133 is the same as that provided to mirror 130 (via mirror 113).

Thus, the fourth harmonic generator 102B operates in a substantially similar manner to the second harmonic generator 102A except that the input wavelength of the light entering the fourth harmonic generator 102B is the second harmonic (e.g. 532 nm) and the output wavelength is the fourth harmonic (e.g. 266 nm). Note that the coatings and materials of the second and fourth harmonic generator components are chosen appropriately for their respective wavelengths.

In some prior art devices (not shown), second modulator 123 is omitted, thereby resulting in both servo controls operating at the same modulation frequency. In other prior art devices (also not shown), neither first modulator 103 nor second modulator 123 is present. For example, IR laser 101 generates a modulated output by operating the laser such that two modes are generated, those two modes being chosen to have a wavelength separation and relative amplitudes such that an appropriately modulated output is generated by the "beating" of the two modes (see, for example, U.S. Published Patent Application 2006/0176916 by Zanger et al.). Another resonant-cavity servo-control method known in the art that does not need to modulate the laser is that first described by Hansch and Couillaud in Optical Communications, 35, 442-444, (1980) which uses polarization to measure the phase change in the resonant cavity.

In yet other prior art devices, one or more harmonic generators may comprise two or three mirrors instead of four. In some embodiments, the two cavities may have a different number of mirrors. In yet other prior art devices, the DUV output wavelength may be separated from the recirculating light by a beam splitter (not shown) placed between NLO crystal 135 and mirror 133 (therefore, mirror 133 can be coated with a material to be reflective only).

Notably, the servo controls shown in FIG. 1 can be effective at correcting slow changes in cavity length due to, for example, temperature changes. They may also be effective at correcting cavity length changes caused by low amplitude, low frequency vibrations. Unfortunately, other factors may degrade the output of a cavity that cannot be corrected simply by adjusting the cavity lengths. These factors can reduce the efficiency of the conversion process and lead to a downward trend of the output laser power over time if uncompensated effects change.

Uncompensated effects can include changes in focal length and astigmatism due to spatially varying changes in the properties of the NLO crystal. Such changes may be reversible when caused by photo-refraction at a location due to the power density of the focused beam at that location, or may be irreversible due to damage done to the material of the NLO crystal.

Unfortunately, DUV CW laser 100 can compensate only for changes in cavity lengths. Thus, DUV CW laser 100 cannot compensate for any changes in focus or astigmatism of the NLO crystals in its first or second cavities. Because strongly focused laser light in each NLO crystal typically induces both reversible and irreversible changes in that NLO crystal, DUV CW laser 100 generally operates below optimal intensity and with a shorter lifetime.

Therefore, a need arises for a DUV CW laser that can compensate for any changes in focus or astigmatism of the NLO crystals in its constituent harmonic generators.

SUMMARY OF THE DISCLOSURE

A laser for generating deep ultra-violet (DUV) continuous wave (CW) light includes a second harmonic generator and a fourth harmonic generator. The second harmonic generator converts light having a fundamental wavelength to light having a second harmonic wavelength. This conversion may be achieved using a resonant cavity or by other means. The fourth harmonic generator converts the light having the second harmonic wavelength to light having a fourth harmonic wavelength.

In a preferred embodiment, the fourth harmonic generator includes a plurality of mirrors, a first non-linear optical (NLO) crystal, and a second NLO crystal. The first NLO crystal generates the light having the fourth harmonic wavelength and is placed in operative relation to the plurality of mirrors. The second harmonic passes through both the first NLO crystal and the second NLO crystal. Notably, the second optical axes of the second NLO crystal are rotated about a direction of propagation of the light having the second harmonic wavelength within the second NLO crystal approximately 90 degrees relative to the first optical axes of the first NLO crystal. The second NLO crystal provides no wavelength conversion.

In one embodiment, each of the first NLO crystal and the second NLO crystal is hydrogen-annealed. In another embodiment, each of the first NLO crystal and the second NLO crystal comprises a hydrogen-annealed CLBO (cesium lithium borate) crystal. The light having the second harmonic may be focused to a substantially elliptical beam waist in, or proximate to, the first NLO crystal, with a long axis of the ellipse substantially in the plane containing the first e-axis. The second NLO crystal may be held at substantially the same temperature as the first NLO crystal. The phase matching angle and temperature of the first NLO crystal may be chosen so as to reduce astigmatism created in the first NLO crystal by a focused beam therein. In one embodiment, at least the first NLO crystal is controlled in temperature (e.g. at approximately 50° C. or lower) to reduce astigmatism created in the first NLO crystal by the focused beam.

The fourth harmonic generator may further include a pair of thin plates with parallel surfaces. The pair of thin plates can be tilted at substantially equal and opposite angles so as to minimize any displacement of a light beam while compensating for astigmatism. The fourth harmonic generator may further include a feedback control loop that automatically adjusts an astigmatism compensation so as to substantially cancel astigmatism introduced by the fourth harmonic generator.

A system for inspecting a wafer, reticle, or photomask is also described. This system may include the DUV CW laser including the first and second NLO crystals in the fourth harmonic generator, as described herein.

A method of generating deep ultra-violet (DUV) continuous wave (CW) light in a laser. This method includes converting light having a fundamental wavelength to light having a second harmonic wavelength as well as converting the light having the second harmonic wavelength to light having a fourth harmonic wavelength using a first non-linear optical (NLO) crystal and a second NLO crystal. Generating the light having the fourth harmonic wavelength includes passing the second harmonic through the first NLO crystal and through the second NLO crystal, and rotating second optical axes of the second NLO crystal about a direction of propagation of the light having the second harmonic wavelength within the second NLO crystal approximately 90 degrees relative to first optical axes of the first NLO crystal. Notably, only the first NLO crystal provides wavelength conversion to the fourth harmonic wavelength.

BRIEF DESCRIPTION OF THE DRAWINGS

FIG. 3 illustrates an end view of an exemplary NLO crystal that can be used in the improved DUV CW laser shown in FIG. 2.

FIG. 4 illustrates the relative orientation of the first and second NLO crystals used in the improved DUV CW laser shown in FIG. 2.

DETAILED DESCRIPTION OF THE DRAWINGS

Figure 1:
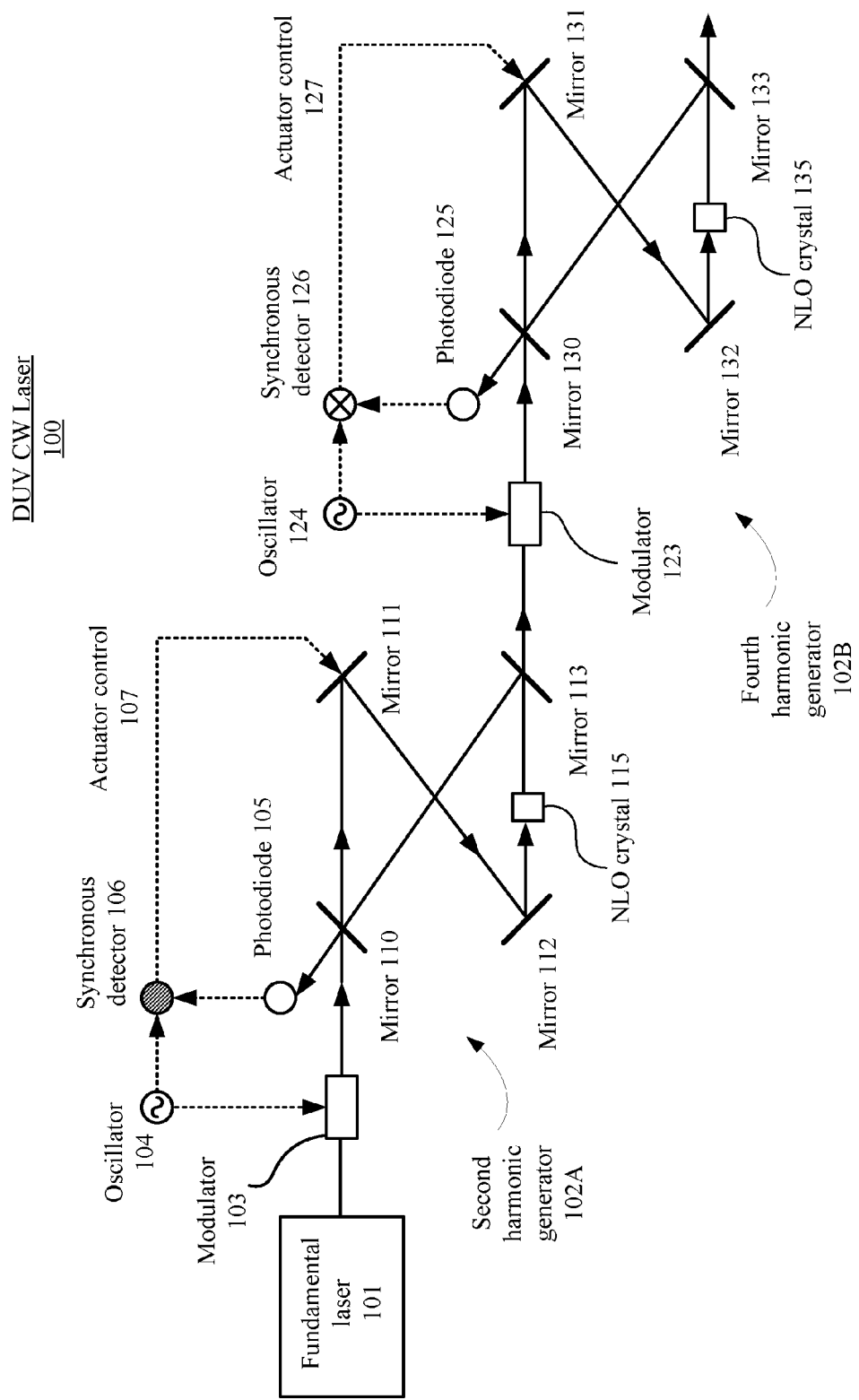
FIG. 1 illustrates a prior art DUV CW laser including a plurality of cavities, each cavity including a plurality of mirrors and an NLO crystal.
Figure 2:
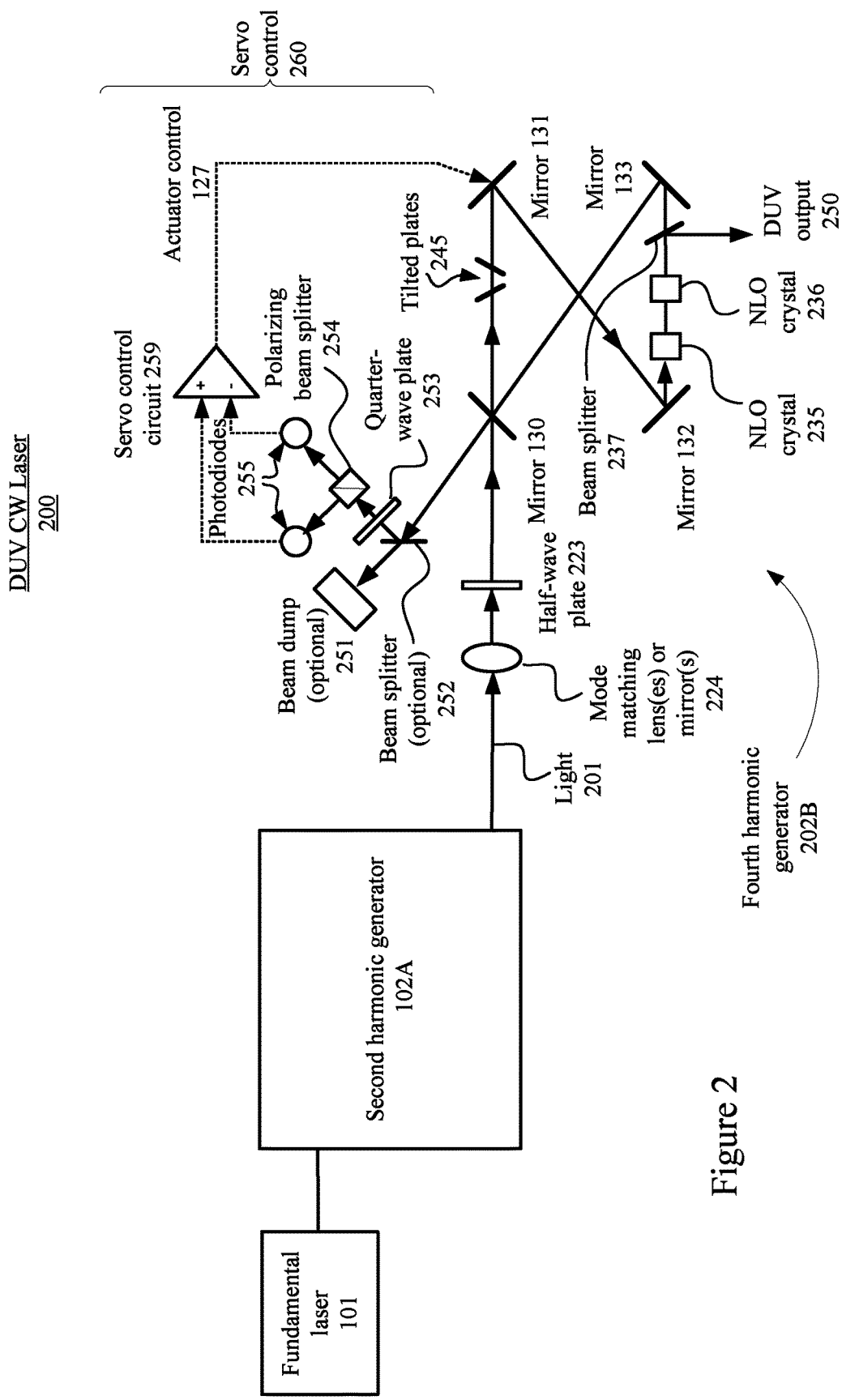
FIG. 2 illustrates an improved DUV CW laser including a plurality of cavities, wherein the second cavity includes two NLO crystals in a predetermined orientation with respect to each other.

As described in detail below, an improved DUV CW laser can include several improvements to the fourth harmonic generator. These improvements may be used in combination or individually. FIG. 2 illustrates an exemplary improved DUV CW laser 200. Note that the elements of FIG. 2 labeled with the same numbers as the corresponding elements of FIG. 1 have the same function as that described in reference to FIG. 1 and such elements may be implemented in a substantially similar manner. For example, in this embodiment, DUV CW laser 200 includes the fundamental laser 101 and the second harmonic generator 102A, both of which are described in detail in reference to FIG. 1.

Referring to FIG. 2, light 201 generated by the second harmonic generator 102A is focused by mode matching lens 224 and enters the fourth-harmonic generator 202B through mirror 130. In one embodiment, the light 201 may be at a wavelength of approximately 532 nm (or another visible wavelength). Light 201 circulates around the fourth-harmonic generator 202B by reflecting from mirrors 130, 131, 132, and 133 (described in reference to FIG. 1). Note that some embodiments of the fourth-harmonic generator 202B may have only two or three mirrors instead of the four shown. Mirrors 130, 131, 132 and 133 are coated so as to be highly reflective at that visible wavelength for the angle of incidence of the circulating light. The coating of mirror 130 must also transmit the light 201 that arrives at a different angle of incidence than the circulating light.

The length of the cavity implementing the fourth harmonic generator 202B may be controlled by any of the locking schemes known in the art (some of which are listed above). In one embodiment, the cavity length of the fourth harmonic generator 202B may be controlled using Hänsch-Couillaud locking scheme (see reference listed above). Note that high visible-light power levels (such as about 10 W or more) can damage a modulator, or a modulator that can withstand such powers may be expensive. The Hänsch-Couillaud locking scheme of fourth harmonic generator 202B can use a half-wave plate 223 oriented so as to rotate the polarization of the light 201 through a small angle (such as an angle less than about 2°). A passive component, such as half-wave plate 223, may be better able to withstand a high visible-light power than an active component such as a modulator. A small portion of the circulating light leaves the fourth harmonic generator 202B via mirror 130 along with a reflected component of the input light with the orthogonal polarization (created by half-wave plate 223) is directed to the servo control 260, which is controls the cavity length. Specifically, servo control 260 can determine whether the length of the fourth harmonic generator 202B needs to be adjusted and, if so, whether the length should be increased or decreased and by how much. Actuator control 127 physically controls the position of mirror 131 to maintain the appropriate length of the second cavity so that the phase of the reflected light from mirror 133 is the same as to the visible light 201 arriving at mirror 130. The light from the cavity may, optionally, be attenuated if necessary by beam splitter 252 and beam dump 251. After any necessary attenuation, the light passes through quarter-wave plate 253 which is oriented with its axis at substantially 45° degrees to the polarization direction of the cavity to make the two orthogonal polarizations interfere with one another. Polarizing beam splitter 254 separates the output of quarter-wave plate 253 into two orthogonal polarizations, which are detected by two photodiodes 255. Optionally linear polarizers (not shown) may be placed in front of the photodiodes 255 if the polarizing beam splitter 254 does not provide sufficient polarization discrimination. Servo control circuit 259 generates the actuator control 127 from the difference of the signals from the two photodiodes.

As noted above, DUV CW laser 200 includes two NLO crystals in the fourth harmonic generator: a first NLO crystal 235 that provides a frequency conversion and a second NLO crystal 236 that provides no frequency conversion. In one embodiment, NLO crystal 235 can generate the fourth harmonic (for example, a wavelength of 266 nm is generated from an input wavelength of 532 nm). In one preferred embodiment, NLO crystal 235 can be implemented by a hydrogen-annealed NLO crystal. An exemplary hydrogen-annealed CLBO (cesium lithium borate) NLO is described in U.S. Published Patent Application 2013/0088706 filed on Jun. 5, 2012, which claims priority to U.S. Provisional Application 61/544,425 filed on Oct. 7, 2011, both of which are incorporated by reference herein. One advantage of using a hydrogen-annealed NLO crystal over a conventional NLO crystal is that the hydrogen-annealed NLO crystal can operate at higher DUV power densities with less, or slower, damage. Thus, a DUV CW laser including at least one hydrogen-annealed NLO crystal can provide more stable output, with longer life and lower operating costs due to increased time intervals between service or repair.

In some preferred embodiments, DUV CW laser 200 can focus light 201 within NLO crystal 235 in an elliptical focus with the long axis of the ellipse oriented substantially parallel to the plane containing the e-axis (extraordinary axis) of the NLO crystal. This orientation is shown in FIG. 3, which shows an end view of NLO crystal 235. As shown in FIG. 3, the light is focused to an elliptical spot 303 in, or proximate to, NLO crystal 235. Notably, the long axis of elliptical spot 303 is aligned substantially parallel to the plane containing the e-axis (i.e. a horizontal plane as depicted in FIG. 3) of NLO crystal 235. In some preferred embodiments, the focus of the shorter axis of elliptical spot 303 is reduced by approximately the same factor as the focus of the long axis is increased so as to approximately maintain the power density and hence conversion efficiency. Elliptical focusing may be achieved by one, or more, of the mode matching lenses or mirrors 224 being cylindrically curved or having different radii of curvature in two different directions. In some embodiments, the second harmonic generator 102A may output an elliptical beam, but not necessarily elongated along the correct axis, or with the desired eccentricity, for the fourth harmonic generator 202B. In one embodiment, a cylindrical telescope or other optics may be used for mode matching lenses or mirrors 224 to reshape and refocus the elliptical spot into the fourth harmonic generator 202B with the desired shape and size.

The strong electric field of the focused laser radiation inside NLO crystal 235 causes a change in the refractive index of the crystal's material (called photorefraction). Because the electric field strength decreases from the center of elliptical spot 303 to its edges, the change in the refractive index is greater at the center of elliptical spot 303 than at its edges. Furthermore, the photorefractive effect is stronger in the direction containing the e-axis.

One advantage of using elliptical focusing with the long axis parallel to the plane containing the e-axis is that walk-off of the output beam occurs in this direction. An elongated ellipse in this direction allows a longer NLO crystal to be used while maintaining beam quality. U.S. patent application Ser. No. 13/412,564, filed by Dribinski et al. on Mar. 2, 2012 and incorporated by reference herein, describes exemplary elliptical focusing of the light in an NLO crystal.

Notably, photorefraction introduces astigmatism into the fourth-harmonic generator cavity. A conventional servo control that controls the cavity length as measured by distances between the mirrors can only correct for the average path length change from the average index change and not for any astigmatism caused by the index change being different at different locations within the focused beam. Second crystal 236 is substantially similar in material composition to the frequency conversion crystal, i.e. first crystal 235, except that its crystal axes are rotated 90° about an axis parallel to the direction of propagation of light 201 and so second crystal 236 performs no frequency conversion. In one embodiment (shown), second NLO crystal 236 is placed immediately downstream of first NLO crystal 235 so that the fourth harmonic light and the residual second harmonic light passes through the second crystal. Since both the second and fourth harmonics contribute to the photorefraction and other non-ideal effects in the NLO crystal, placing the second NLO crystal 236 downstream of the first NLO crystal 235 ensures that the aberrations created by the second NLO crystal 236 are substantially similar to those created by the first NLO crystal 235, except that they are rotated through 90°. In other embodiments, second NLO crystal 236 is placed immediately upstream (not shown) of first NLO crystal 235 so that the second NLO crystal 236 is not subjected to the fourth harmonic (UV) light. Since the power density of the second harmonic in the resonant cavity is much greater than that of the fourth harmonic, most of the photorefractive effects are generated by the second harmonic, and so the aberrations in the second NLO crystal 236 may be similar enough to those in the first NLO crystal 235 (other than the 90° rotation) to substantially cancel the astigmatism created in the first NLO crystal 235. The advantage of placing the second NLO crystal 236 upstream of the first NLO crystal 235 is that the second NLO crystal will have a longer lifetime if it is not exposed to the fourth harmonic UV radiation which can degrade the NLO crystal. In such a case, the second NLO crystal 236 would need replacing less frequently (or not at all) and therefore the cost of maintenance for the laser over multiple years would be lower. In some embodiments, if the light circulating in the fourth harmonic generator 202B is refocused at a specific point in the cavity, then first NLO crystal 235 could be placed at that location instead of immediately adjacent to second NLO crystal 236.

In one embodiment, the first and second NLO crystals in the fourth harmonic generator 202B have their input and output surfaces cut at approximately Brewster's angle relative to the incident visible light with the surface oriented so that the incident visible light is substantially p polarized with respect to that surface. As is well known to one skilled in the appropriate arts, a Brewster-cut surface has substantially zero reflectivity for p polarized light. The use of a Brewster-cut surface eliminates the need for an anti-reflection coating on the surfaces of the NLO crystal. Anti-reflection coatings that can withstand the high power densities inside the fourth-harmonic generator cavity may not be available. Since the fourth harmonic has its polarization perpendicular to the polarization of the visible light, the fourth harmonic will not have low reflectivity from a surface that is Brewster cut for the visible. Hence if Brewster cut crystals are used, it is preferred to place the second NLO crystal 236 upstream of the first NLO crystal 235 to avoid the loss of fourth harmonic radiation.

The purpose of second NLO crystal 236 is to substantially cancel the astigmatism caused by first NLO crystal 235. To achieve this purpose, in one embodiment, second NLO crystal 236 is oriented so that its optical axes are rotated substantially 90° about the direction of propagation of the light with respect to the optical axes of the first NLO crystal 235. Because the astigmatism introduced by second NLO crystal 236 is substantially rotated by 90° with respect to first NLO crystal 235, the two astigmatisms substantially cancel each other. Even though including second NLO crystal 236 increases the cost of DUV CW laser 200, that cost increase can be offset by the higher performance, longer life, and reduced frequency of service compared with a laser using a single crystal in the fourth harmonic generator (see, e.g. FIG. 1). The relative orientation of the optical axes of NLO crystals 235 and 236 is shown in FIG. 4. The e-axis of the first NLO crystal 235 is aligned relative to direction of propagation and polarization of the incoming light 410 (i.e. the second harmonic) so as to achieve phase matching for generation of the fourth harmonic from the second harmonic at desired crystal temperature. For example, if the NLO crystals comprise CLBO, the desired operating temperature of the CLBO is approximately 50° C., and the second harmonic is at a wavelength of 532 nm, then the e-axis of the crystal should be at substantially 61.6° relative to the direction of propagation of the incoming light and should be perpendicular to the direction of polarization of the incoming light. FIG. 4 shows, for purposes of illustration, the e-axis lying in a substantially horizontal direction at an angle relative to the direction of propagation of the light. As shown, second NLO crystal 236 is oriented with the plane containing its e-axis and the direction of propagation of the light substantially vertical (the e-axis being in direction 408) which is substantially perpendicular to the orientation of the plane containing the e-axis and the direction of propagation of the light (the e-axis being in direction 405) of first NLO crystal 235. The angle between the direction of the e-axis 408 and the direction of propagation of the light in the second NLO crystal 236 is substantially equal in value to the angle between the direction of the e-axis 405 and the direction of the light in the first NLO crystal 235, but the orientation of the crystal axes of the two crystals are rotated by 90° relative to one another about the direction of propagation of the incoming light 410.

If the NLO crystals are biaxially birefringent, instead of uniaxially birefringent as in the previous example, the same principles still hold. The optical axes of the first NLO crystal 235 must be orientated aligned relative to direction of propagation and polarization of the incoming light 410 (second harmonic) so as to achieve phase matching for generation of the fourth harmonic from the second harmonic at desired crystal temperature. The second NLO crystal 236 must be oriented with its optical axes rotated 90° about the direction of propagation of the incoming light 410.

Referring back to FIG. 2, in some embodiments, one or more of the mirrors 130, 131, 132 and 133 is a spherical mirror to refocus light circulating in the fourth harmonic generator 202B to a beam waist substantially inside, or proximate to, first NLO crystal 235. In some embodiments, one or more of the mirrors 130, 131, 132 and 133 is cylindrical to approximately compensate for the astigmatism of first NLO crystal 235. This cylindrical mirror may be used instead or, or in addition to, tilted plates 245, or second NLO crystal 236. In some embodiments, an actuator (not shown) can control the curvature of the cylindrical mirror to adjust the astigmatism compensation. In some embodiments, an actuator (not shown) can change the curvature in one direction of a spherical mirror in order to compensate for astigmatism. One skilled in the art would understand how to choose the mirror curvatures to focus the circulating light into a circular or elliptical focus as well as to correct for astigmatism.

One skilled in the appropriate arts would understand that other astigmatism control devices and methods could be substituted for those described above and would be within the scope of this invention.

In some preferred embodiments, the operating temperature of at least NLO crystal 235 is controlled to minimize astigmatism. For CLBO, this means operating NLO crystal 235 at a low temperature, preferably less than about 100° C., or in some embodiments, less than about 50° C., or less than about 30° C. The change in index of CLBO and some other NLO crystal materials caused by the focused light is less at a lower temperature than at a higher temperature.

To operate NLO crystal 235 at a temperature substantially less than 100° C., in one embodiment, the fourth harmonic generator 202B (which includes its constituent mirrors and NLO crystals) can be contained in a protected low humidity environment. This environment is to prevent moisture being absorbed by NLO crystal 235 and NLO crystal 236. Moisture degrades performance and lifetime of most NLO crystal materials, particularly when generating DUV wavelengths. Thus, NLO crystals 235 and 236 should be held at approximately the same temperature so that approximately similar amounts of astigmatism are generated in each crystal.

In some embodiments, DUV CW laser 200 can include two tilted thin plates 245, each with parallel planar surfaces, disposed in operative relation to first NLO crystal 235 such that light circulated in the fourth harmonic generator passes through the parallel planar surfaces of both thin plates 245. A single tilted thin plate placed in the light path introduces astigmatism, and also displaces the light beam. However, two plates 245 disposed in a tilted arrangement such as that depicted in FIG. 2 (i.e., such that the two plates are tilted by equal, but opposite, amounts about parallel axes), introduce astigmatism without displacing the beam. Thus, tilted plates 245 can be adjusted to substantially correct for the astigmatism introduced by first NLO crystal 235 when second NLO crystal 236 is not used or may correct for any residual astigmatism not corrected (or overcorrected) by second NLO crystal 236. Thus, tilted plates 245 may be used instead of, or in addition to, second NLO crystal 236.

In one embodiment a Brewster-cut NLO crystal (for at least the first NLO crystal 235) is used with the two tilted plates 245. The input and output surfaces of the NLO crystal are cut so that the input light is incident at close to Brewster's angle with the polarization of the input light substantially p polarized relative to that surface so that there is minimal reflection of the visible light at either surface of the NLO crystal.

In some embodiments, tilted plates 245 remain fixed in predetermined tilt angles during operation of the laser. In other embodiments, the tilt angles may be adjusted to compensate for the reversible astigmatism that is caused by first NLO crystal 235. In yet other embodiments, the astigmatism in the fourth harmonic generator 202B is monitored by a sensor (not shown), which generates a signal that adjusts tilted plates 245 to substantially cancel the astigmatism.

In one embodiment, the DUV output of the second cavity may be separated from light 201 by a beam splitter 237 (as shown in FIG. 2), or by appropriate coatings on mirror 133. Because the DUV and visible light have substantially orthogonal polarizations to each other, beam splitter 237 may be a polarizing beam splitter such as, for example, one oriented at a Brewster angle relative to the light 201. Alternatively, beam splitter 237 may have a coating that preferentially reflects the DUV wavelength while transmitting the visible wavelength.

FIGS. 5-12 illustrate systems that can include the above-described improved DUV CW laser (also called an illumination or light source at a system level). These systems can be used in photomask, reticle, or wafer inspection applications.

Figure 5:
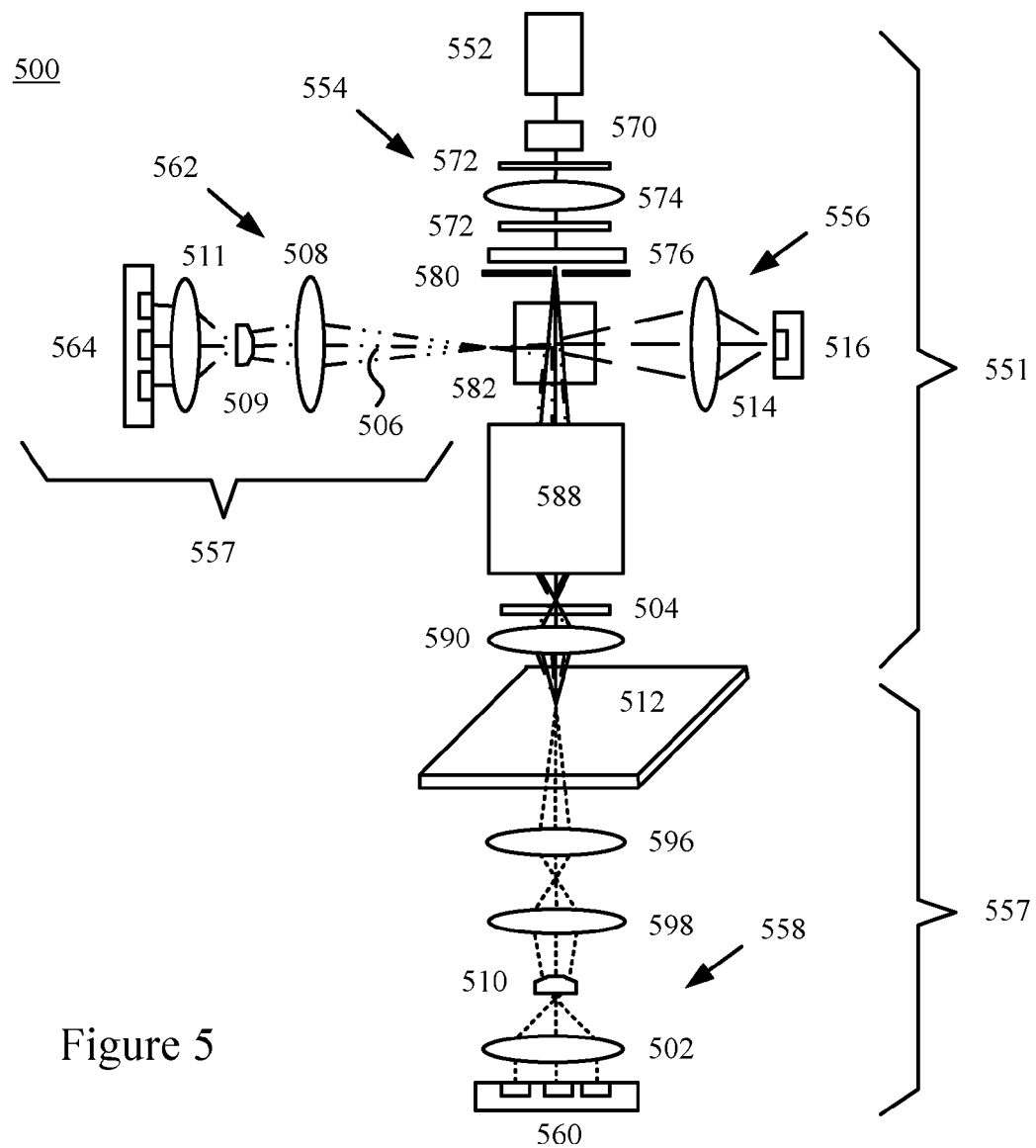
FIGS. 5-12 illustrate systems that can include the described improved DUV CW laser. These systems can be used in photomask, reticle, or wafer inspection applications.

FIG. 5 illustrates an exemplary optical inspection system 500 for inspecting the surface of a substrate 512. System 500 generally includes a first optical arrangement 551 and a second optical arrangement 557. As shown, first optical arrangement 551 includes at least a light source 552, inspection optics 554, and reference optics 556, while the second optical arrangement 557 includes at least transmitted light optics 558, transmitted light detectors 560, reflected light optics 562, and reflected light detectors 564. In one preferred configuration, light source 552 includes the above-described improved DUV CW illumination sources.

Light source 552 is configured to emit a light beam that passes through an acousto-optic device 570, which is arranged for deflecting and focusing the light beam. Acousto-optic device 570 may include a pair of acousto-optic elements, e.g. an acousto-optic pre-scanner and an acousto-optic scanner, which deflect the light beam in the Y-direction and focus it in the Z-direction. By way of example, most acousto-optic devices operate by sending an RF signal to quartz or a crystal such as $TeO_2$. This RF signal causes a sound wave to travel through the crystal. Because of the travelling sound wave, the crystal becomes asymmetric, which causes the index of refraction to change throughout the crystal. This change causes incident beams to form a focused travelling spot which is deflected in an oscillatory fashion.

When the light beam emerges from acousto-optic device 570, it then passes through a pair of quarter wave plates 572 and a relay lens 574. Relay lens 574 is arranged to collimate the light beam. The collimated light beam then continues on its path until it reaches a diffraction grating 576. Diffraction grating 576 is arranged for flaring out the light beam, and more particularly for separating the light beam into three distinct beams, which are spatially distinguishable from one another (i.e. spatially distinct). In most cases, the spatially distinct beams are also arranged to be equally spaced apart and have substantially equal light intensities.

Upon leaving the diffraction grating 576, the three beams pass through an aperture 580 and then continue until they reach a beam splitter cube 582. Beam splitter cube 582 (in combination with the quarter wave plates 572) is arranged to divide the beams into two paths, i.e. one directed downward and the other directed to the right (in the configuration shown in FIG. 5). The path directed downward is used to distribute a first light portion of the beams to substrate 512, whereas the path directed to the right is used to distribute a second light portion of the beams to reference optics 556. In most embodiments, most of the light is distributed to substrate 512 and a small percentage of the light is distributed to reference optics 556, although the percentage ratios may vary according to the specific design of each optical inspection system. In one embodiment, reference optics 556 can include a reference collection lens 514 and a reference detector 516. Reference collection lens 514 is arranged to collect and direct the portion of the beams on reference detector 516, which is arranged to measure the intensity of the light. Reference optics are generally well known in the art and for the sake of brevity will not be discussed in detail.

The three beams directed downward from beam splitter 582 are received by a telescope 588, which includes several lens elements that redirect and expand the light. In one embodiment, telescope 588 is part of a telescope system that includes a plurality of telescopes rotating on a turret. For example, three telescopes may be used. The purpose of these telescopes is to vary the size of the scanning spot on the substrate and thereby allow selection of the minimum detectable defect size. More particularly, each of the telescopes generally represents a different pixel size. As such, one telescope may generate a larger spot size making the inspection faster and less sensitive (e.g., low resolution), while another telescope may generate a smaller spot size making inspection slower and more sensitive (e.g., high resolution).

From telescope 588, the three beams pass through an objective lens 590, which is arranged for focusing the beams onto the surface of substrate 512. As the beams intersect the surface as three distinct spots, both reflected light beams and transmitted light beams may be generated. The transmitted light beams pass through substrate 512, while the reflected light beams reflect off the surface. By way of example, the reflected light beams may reflect off of opaque surfaces of the substrate, and the transmitted light beams may transmit through transparent areas of the substrate. The transmitted light beams are collected by transmitted light optics 558 and the reflected light beams are collected by reflected light optics 562.

With regards to transmitted light optics 558, the transmitted light beams, after passing through substrate 512, are collected by a first transmitted lens 596 and focused with the aid of a spherical aberration corrector lens 598 onto a transmitted prism 510. Prism 510 can be configured to have a facet for each of the transmitted light beams that are arranged for repositioning and bending the transmitted light beams. In most cases, prism 510 is used to separate the beams so that they each fall on a single detector in transmitted light detector arrangement 560 (shown as having three distinct detectors). Accordingly, when the beams leave prism 510, they pass through a second transmitted lens 502, which individually focuses each of the separated beams onto one of the three detectors, each of which is arranged for measuring the intensity of the transmitted light.

With regards to reflected light optics 562, the reflected light beams after reflecting off of substrate 512 are collected by objective lens 590, which then directs the beams towards telescope 588. Before reaching telescope 588, the beams also pass through a quarter wave plate 504. In general terms, objective lens 590 and telescope 588 manipulate the collected beams in a manner that is optically reverse in relation to how the incident beams are manipulated. That is, objective lens 590 re-collimates the beams, and telescope 888 reduces their size. When the beams leave telescope 588, they continue (backwards) until they reach beam splitter cube 582. Beam splitter 582 is configured to work with quarter wave-plate 504 to direct the beams onto a central path 506.

The beams continuing on path 506 are then collected by a first reflected lens 508, which focuses each of the beams onto a reflected prism 509, which includes a facet for each of the reflected light beams. Reflected prism 509 is arranged for repositioning and bending the reflected light beams. Similar to transmitted prism 510, reflected prism 509 is used to separate the beams so that they each fall on a single detector in the reflected light detector arrangement 564. As shown, reflected light detector arrangement 564 includes three individually distinct detectors. When the beams leave reflected prism 509, they pass through a second reflected lens 511, which individually focuses each of the separated beams onto one of these detectors, each of which is arranged for measuring the intensity of the reflected light.

There are multiple inspection modes that can be facilitated by the aforementioned optical assembly. By way of example, the optical assembly can facilitate a transmitted light inspection mode, a reflected light inspection mode, and a simultaneous inspection mode. With regards to the transmitted light inspection mode, transmission mode detection is typically used for defect detection on substrates such as conventional optical masks having transparent areas and opaque areas. As the light beams scan the mask (or substrate 512), the light penetrates the mask at transparent points and is detected by the transmitted light detectors 560, which are located behind the mask and which measure the intensity of each of the light beams collected by transmitted light optics 558 including first transmitted lens 596, second transmitted lens 502, spherical aberration lens 598, and prism 510.

With regards to the reflected light inspection mode, reflected light inspection can be performed on transparent or opaque substrates that contain image information in the form of chromium, developed photoresist or other features. Light reflected by the substrate 512 passes backwards along the same optical path as inspection optics 554, but is then diverted by a polarizing beam splitter 582 into detectors 564. More particularly, first reflected lens 508, prism 509, and second reflected lens 511 project the light from the diverted light beams onto detectors 564. Reflected light inspection may also be used to detect contamination on top of opaque substrate surfaces.

With regards to the simultaneous inspection mode, both transmitted light and reflected light are utilized to determine the existence and/or type of a defect. The two measured values of the system are the intensity of the light beams transmitted through substrate 512 as sensed by transmitted light detectors 860 and the intensity of the reflected light beams as detected by reflected light detectors 564. Those two measured values can then be processed to determine the type of defect, if any, at a corresponding point on substrate 512.

More particularly, simultaneous transmitted and reflected detection can disclose the existence of an opaque defect sensed by the transmitted detectors while the output of the reflected detectors can be used to disclose the type of defect. As an example, either a chrome dot or a particle on a substrate may both result in a low transmitted light indication from the transmission detectors, but a reflective chrome defect may result in a high reflected light indication and a particle may result in a lower reflected light indication from the same reflected light detectors. Accordingly, by using both reflected and transmitted detection one may locate a particle on top of chrome geometry which could not be done if only the reflected or transmitted characteristics of the defect were examined. In addition, one may determine signatures for certain types of defects, such as the ratio of their reflected and transmitted light intensities. This information can then be used to automatically classify defects. U.S. Pat. No. 5,563,702, which issued on Oct. 8, 1996 and is incorporated by reference herein, describes additional details regarding system 500.

In accordance with certain embodiments of the present invention, an inspection system that incorporates a laser system may simultaneously detect two channels of data on a single detector. Such an inspection system may be used to inspect a substrate such as a reticle, a photomask or a wafer, and may operate as described in U.S. Pat. No. 7,528,943, which issued on May 5, 2009 to Brown et al, and is incorporated by reference herein.

Figure 6:
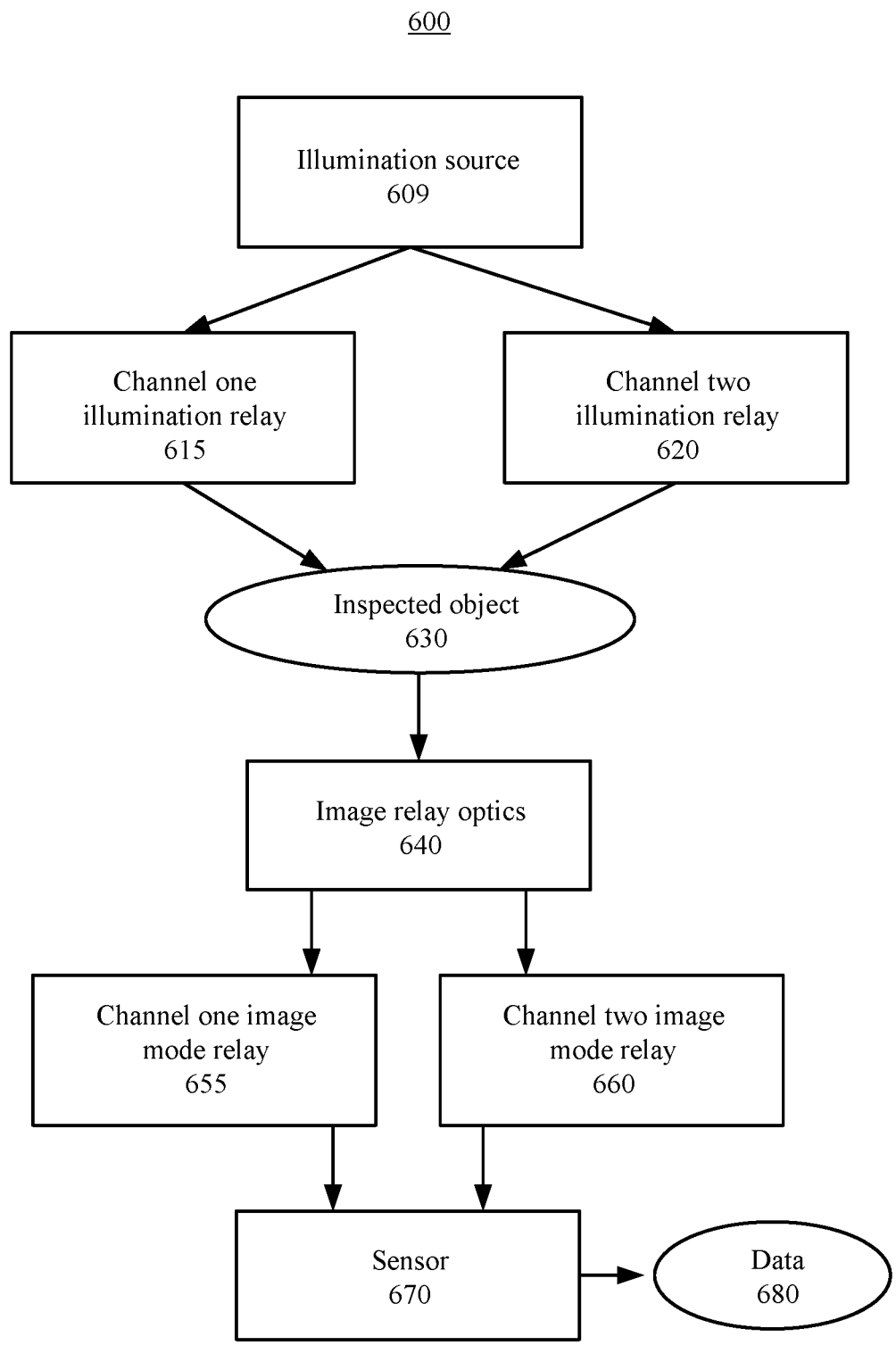

FIG. 6 shows a reticle, photomask or wafer inspection system 600 that simultaneously detects two channels of image or signal on one sensor 670. The illumination source 609 incorporates an improved DUV CW laser, as described herein, and may further comprise a coherence reducing scheme. The two channels may comprise reflected and transmitted intensity when an inspected object 630 is transparent (for example a reticle or photomask), or may comprise two different illumination modes, such as angles of incidence, polarization states, wavelength ranges or some combination thereof.

As shown in FIG. 6, illumination relay optics 615 and 620 relay the illumination from source 609 to the inspected object 630. The inspected object 630 may be a reticle, a photomask, a semiconductor wafer or other article to be inspected. Image relay optics 640, 655 and 660 relay the light that is reflected and/or transmitted by the inspected object 630 to the sensor 670. The data corresponding to the detected signals or images for the two channels is shown as data 680 and is transmitted to a computer (not shown) for processing.

Figure 7:
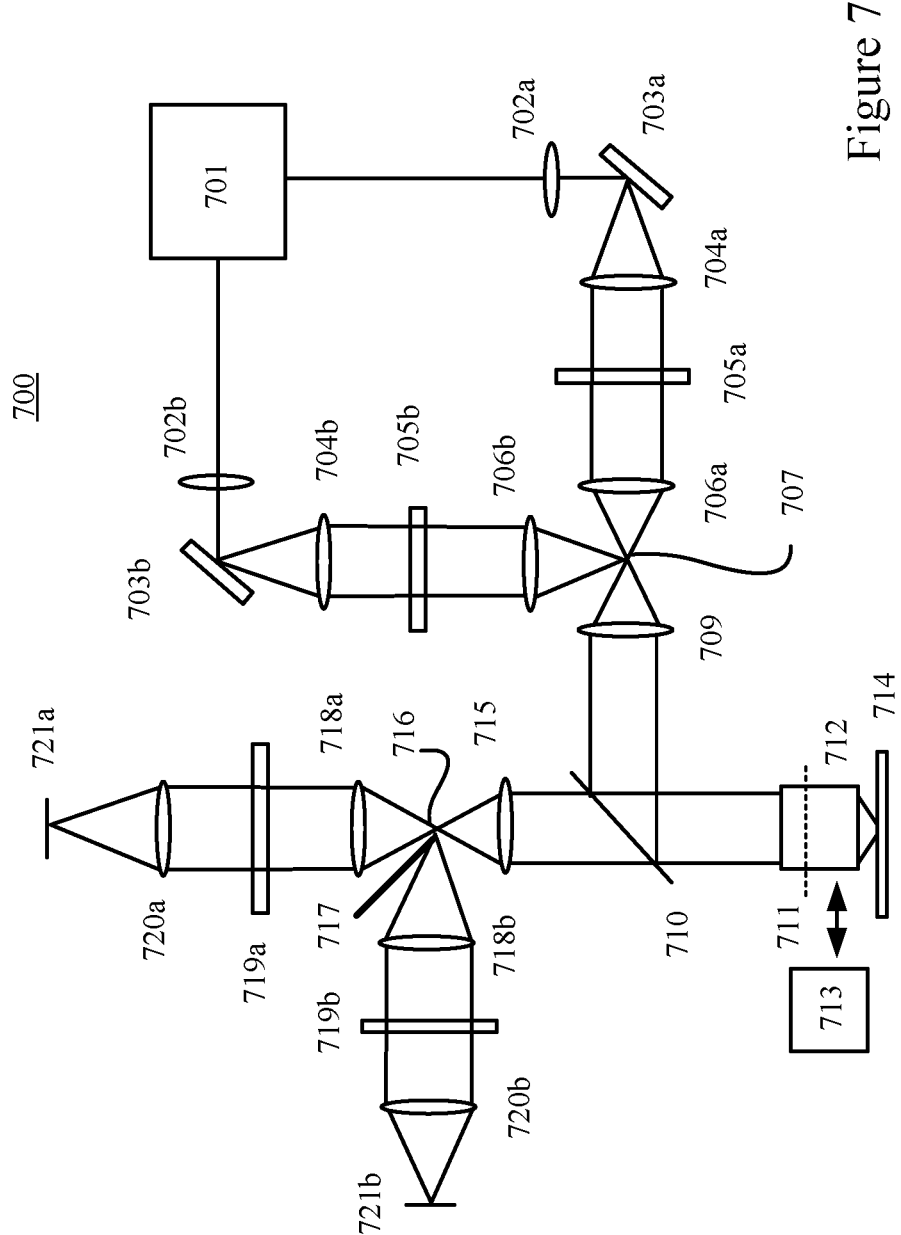

FIG. 7 illustrates an exemplary inspection system 700 including multiple objectives and one of the above-described improved DUV CW lasers. In system 700, illumination from a laser 701, which incorporates one of the UV lasers described herein, is sent to multiple sections of the illumination subsystem. A first section of the illumination subsystem includes elements 702a through 706a. Lens 702a focuses light from laser 701. Light from lens 702a then reflects from mirror 703a. Mirror 703a is placed at this location for the purposes of illustration, and may be positioned elsewhere. Light from mirror 703a is then collected by lens 704a, which forms illumination pupil plane 705a. An aperture, filter, or other device to modify the light may be placed in pupil plane 705a depending on the requirements of the inspection mode. Light from pupil plane 705a then passes through lens 706a and forms illumination field plane 707.

A second section of the illumination subsystem includes elements 702b through 706b. Lens 702b focuses light from laser 701. Light from lens 702b then reflects from mirror 703b. Light from mirror 703b is then collected by lens 704b which forms illumination pupil plane 705b. An aperture, filter, or other device to modify the light may be placed in pupil plane 705b depending on the requirements of the inspection mode. Light from pupil plane 705b then passes through lens 706b and forms illumination field plane 707. The light from the second section is then redirected by mirror or reflective surface such that the illumination field light energy at illumination field plane 707 is comprised of the combined illumination sections.

Field plane light is then collected by lens 709 before reflecting off a beamsplitter 710. Lenses 706a and 709 form an image of first illumination pupil plane 1005a at objective pupil plane 711. Likewise, lenses 706b and 709 form an image of second illumination pupil plane 705b at objective pupil plane 711. An objective 712 (or alternatively 713) then takes the pupil light and forms an image of illumination field 707 at sample 714. Objective 712 or objective 713 can be positioned in proximity to sample 714. Sample 714 can move on a stage (not shown), which positions the sample in the desired location. Light reflected and scattered from the sample 714 is collected by the high NA catadioptric objective 712 or objective 713. After forming a reflected light pupil at objective pupil plane 711, light energy passes beamsplitter 710 and lens 715 before forming an internal field 716 in the imaging subsystem. This internal imaging field is an image of sample 714 and correspondingly illumination field 707. This field may be spatially separated into multiple fields corresponding to the illumination fields. Each of these fields can support a separate imaging mode.

One of these fields can be redirected using mirror 717. The redirected light then passes through lens 718b before forming another imaging pupil 719b. This imaging pupil is an image of pupil 711 and correspondingly illumination pupil 705b. An aperture, filter, or other device to modify the light may be placed in pupil plane 719b depending on the requirements of the inspection mode. Light from pupil plane 719b then passes through lens 720b and forms an image on sensor 721b. In a similar manner, light passing by mirror or reflective surface 717 is collected by lens 718a and forms imaging pupil 719a. Light from imaging pupil 719a is then collected by lens 720a before forming an image on detector 721a. Light imaged on detector 721a can be used for a different imaging mode from the light imaged on sensor 721b.

The illumination subsystem employed in system 700 is composed of laser source 701, collection optics 702-704, beam shaping components placed in proximity to a pupil plane 705, and relay optics 706 and 709. An internal field plane 707 is located between lenses 706 and 709. In one preferred configuration, laser 701 can include one of the above-described improved DUV CW lasers.

With respect to laser 701, while illustrated as a single uniform block having two points or angles of transmission, in reality this represents a laser source able to provide two channels of illumination, for example a first channel of light energy such as laser light energy at a first frequency which passes through elements 702a-706a, and a second channel of light energy such as laser light energy at a second frequency which passes through elements 702b-706b. Different light energy modes may be employed, such as bright field energy in one channel and a dark field mode in the other channel.

While light energy from laser source 701 is shown to be emitted 90 degrees apart, and the elements 702a-706a and 702b-706b are oriented at 90 degree angles, in reality light may be emitted at various orientations, not necessarily in two dimensions, and the components may be oriented differently than as shown. FIG. 7 is therefore simply a representation of the components employed and the angles or distances shown are not to scale nor specifically required for the design.

Elements placed in proximity to pupil plane 705 may be employed in the current system using the concept of aperture shaping. Using this design, uniform illumination or near uniform illumination may be realized, as well as individual point illumination, ring illumination, quadrapole illumination, or other desirable patterns.

Various implementations for the objectives may be employed in a general imaging subsystem. A single fixed objective may be used. The single objective may support all the desired imaging and inspection modes. Such a design is achievable if the imaging system supports a relatively large field size and relatively high numerical aperture. Numerical aperture can be reduced to a desired value by using internal apertures placed at the pupil planes 705a, 705b, 719a, and 719b.

Multiple objectives may also be used as shown in FIG. 7. For example, although two objectives 712 and 713 are shown, any number is possible. Each objective in such a design may be optimized for each wavelength produced by laser 701. These objectives 712 and 713 can either have fixed positions or be moved into position in proximity to the sample 714. To move multiple objectives in proximity to the sample, rotary turrets may be used as are common on standard microscopes. Other designs for moving objectives in proximity of a sample are available, including but not limited to translating the objectives laterally on a stage, and translating the objectives on an arc using a goniometer. In addition, any combination of fixed objectives and multiple objectives on a turret can be achieved in accordance with the present system.

The maximum numerical apertures of this configuration may approach or exceed 0.97, but may in certain instances be higher. The wide range of illumination and collection angles possible with this high NA catadioptric imaging system, combined with its large field size allows the system to simultaneously support multiple inspection modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples.

The imaging subsystem also includes intermediate image forming optics 715. The purpose of the image forming optics 715 is to form an internal image 716 of sample 714. At this internal image 716, a mirror 717 can be placed to redirect light corresponding to one of the inspection modes. It is possible to redirect the light at this location because the light for the imaging modes are spatially separate. The image forming optics 718 (718a and 718b) and 720 (720a and 720b) can be implemented in several different forms including a varifocal zoom, multiple afocal tube lenses with focusing optics, or multiple image forming mag tubes. U.S. Published Application 2009/0180176, which published on Jul. 16, 2009 and is incorporated by reference herein, describes additional details regarding system 700.

Figure 8:
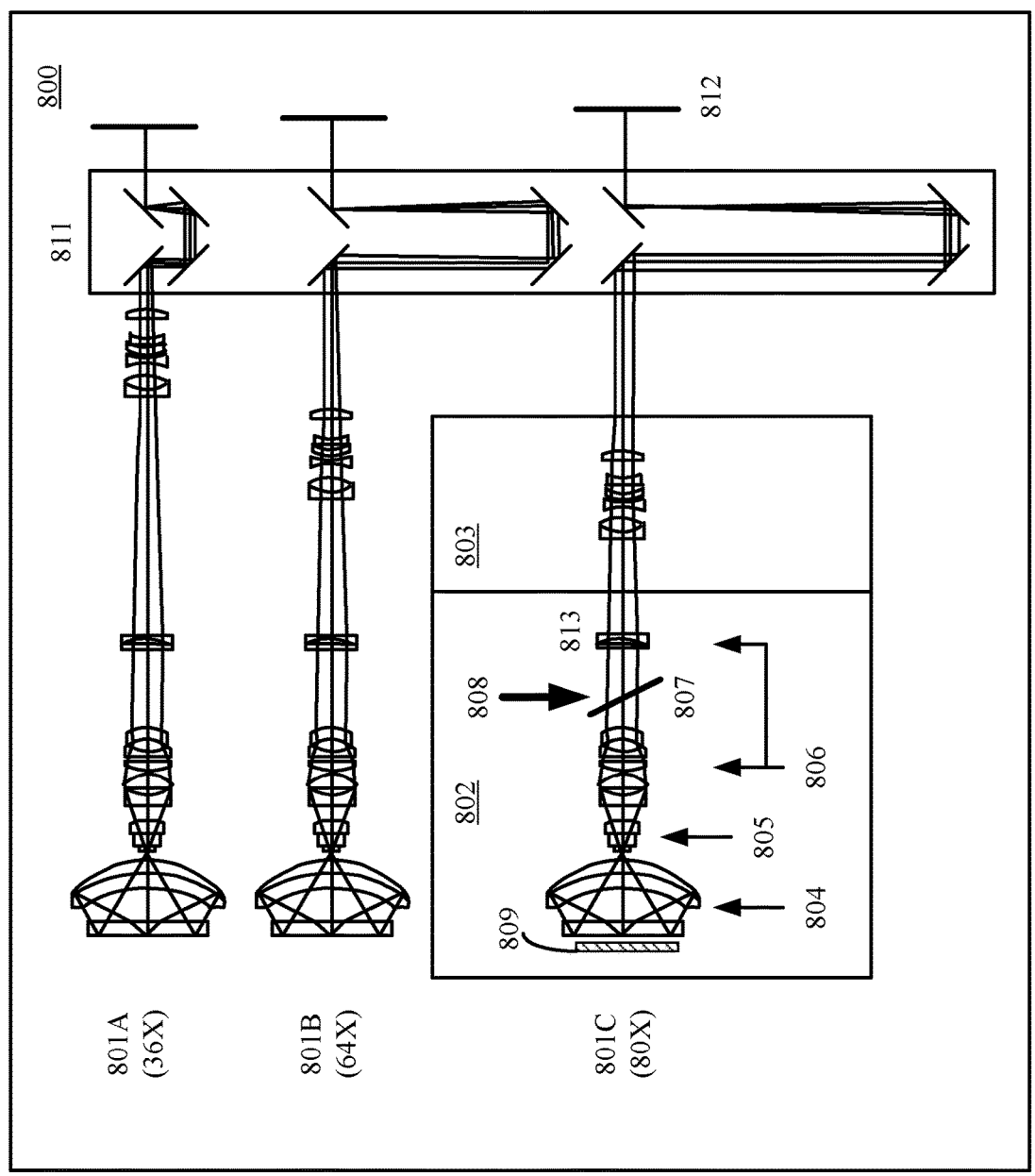

FIG. 8 illustrates an exemplary ultra-broadband UV microscope imaging system 800 with an adjustable magnification. FIG. 8 illustrates three different magnifications of the microscope: 36× with the optics configured as shown as 801A, 64× with the optics configured as shown as 801B, and 80× with the optics configured as shown as 801C. As shown at 801C, the optics include a catadioptric objective section 802 and a zooming tube lens 803. Catadioptric objective section 802 includes a catadioptric lens group 804, a field lens group 805, and a focusing lens group 806. System 800 can image an object/sample 809 (e.g. a wafer being inspected) to an image plane 812.

Catadioptric lens group 804 includes a near planar (or planar) reflector (which is a reflectively coated lens element), a meniscus lens (which is a refractive surface), and a concave spherical reflector. Both reflective elements can have central optical apertures without reflective material to allow light from an intermediate image plane to pass through the concave spherical reflector, be reflected by the near planar (or planar) reflector onto the concave spherical reflector, and pass back through the near planar (or planar) reflector, traversing the associated lens element or elements on the way. Catadioptric lens group 804 is positioned to form a real image of the intermediate image, such that, in combination with zooming tube lens 803, primary longitudinal color of the system is substantially corrected over the wavelength band.

Field lens group 805 can be made from two or more different refractive materials, such as fused silica and fluoride glass, or diffractive surfaces. Field lens group 805 may be optically coupled together or alternatively may be spaced slightly apart in air. Because fused silica and fluoride glass do not differ substantially in dispersion in the deep ultraviolet range, the individual powers of the several component element of the field lens group need to be of high magnitude to provide different dispersions. Field lens group 805 has a net positive power aligned along the optical path proximate to the intermediate image. Use of such an achromatic field lens allows the complete correction of chromatic aberrations including at least secondary longitudinal color as well as primary and secondary lateral color over an ultra-broad spectral range. In one embodiment, only one field lens component need be of a refractive material different than the other lenses of the system.

Focusing lens group 806 includes multiple lens elements, preferably all formed from a single type of material, with refractive surfaces having curvatures and positions selected to correct both monochromatic aberrations and chromatic variation of aberrations and focus light to an intermediate image. In one embodiment of focusing lens group 806, a combination of lenses 813 with low power corrects for chromatic variation in spherical aberration, coma, and astigmatism. A beam splitter 807 provides an entrance for a UV light source 808. UV light source 808 can advantageously be implemented by one of the above-described improved DUV CW lasers.

Zooming tube lens 803 can be all the same refractive material, such as fused silica, and is designed so that primary longitudinal and primary lateral colors do not change during zooming. These primary chromatic aberrations do not have to be corrected to zero, and cannot be if only one glass type is used, but they have to be stationary, which is possible. Then the design of the catadioptric objective section 802 must be modified to compensate for these uncorrected but stationary chromatic aberrations of zooming tube lens 803. Zooming tube lens 803, which can zoom or change magnification without changing its higher-order chromatic aberrations, includes lens surfaces disposed along an optical path of the system.

In one preferred embodiment, zooming tube lens 803 is first corrected independently of catadioptric objective 802 section using two refractive materials (such as fused silica and calcium fluoride). Zooming tube lens 803 is then combined with catadioptric objective section 802, at which time catadioptric objective section 802 can be modified to compensate for the residual higher-order chromatic aberrations of system 800. This compensating is possible because of field lens group 805 and low power lens group 813. The combined system is then optimized with all parameters being varied to achieve the best performance.

System 800 includes a folding mirror group 811 to provide linear zoom motion that allows a zoom from 36× to 100×. Three different positions of the folding mirror group are shown corresponding to three different magnifications 36×, 64× and 80×. The wide range zoom provides continuous magnification change, whereas the fine zoom reduces aliasing and allows electronic image processing, such as cell-to-cell subtraction for a repeating image array. Folding mirror group 811 can be characterized as a "trombone" system of reflective elements. Zooming is done by moving the group of zooming tube lens 803, as a unit, and also moving the arm of the trombone slide as shown in FIG. 8. Because the trombone motion only affects focus, and because the f# speed at its location is very slow, the accuracy of this motion could be very loose. One advantage of this trombone configuration is that it significantly shortens the system. Another advantage is that there is only one zoom motion that involves active (non-flat) optical elements. And the other zoom motion, with the trombone slide, is insensitive to errors. U.S. Pat. No. 5,999,310, which issued on Dec. 7, 1999 and is incorporated by reference herein, describes system 800 in further detail.

Figure 9:
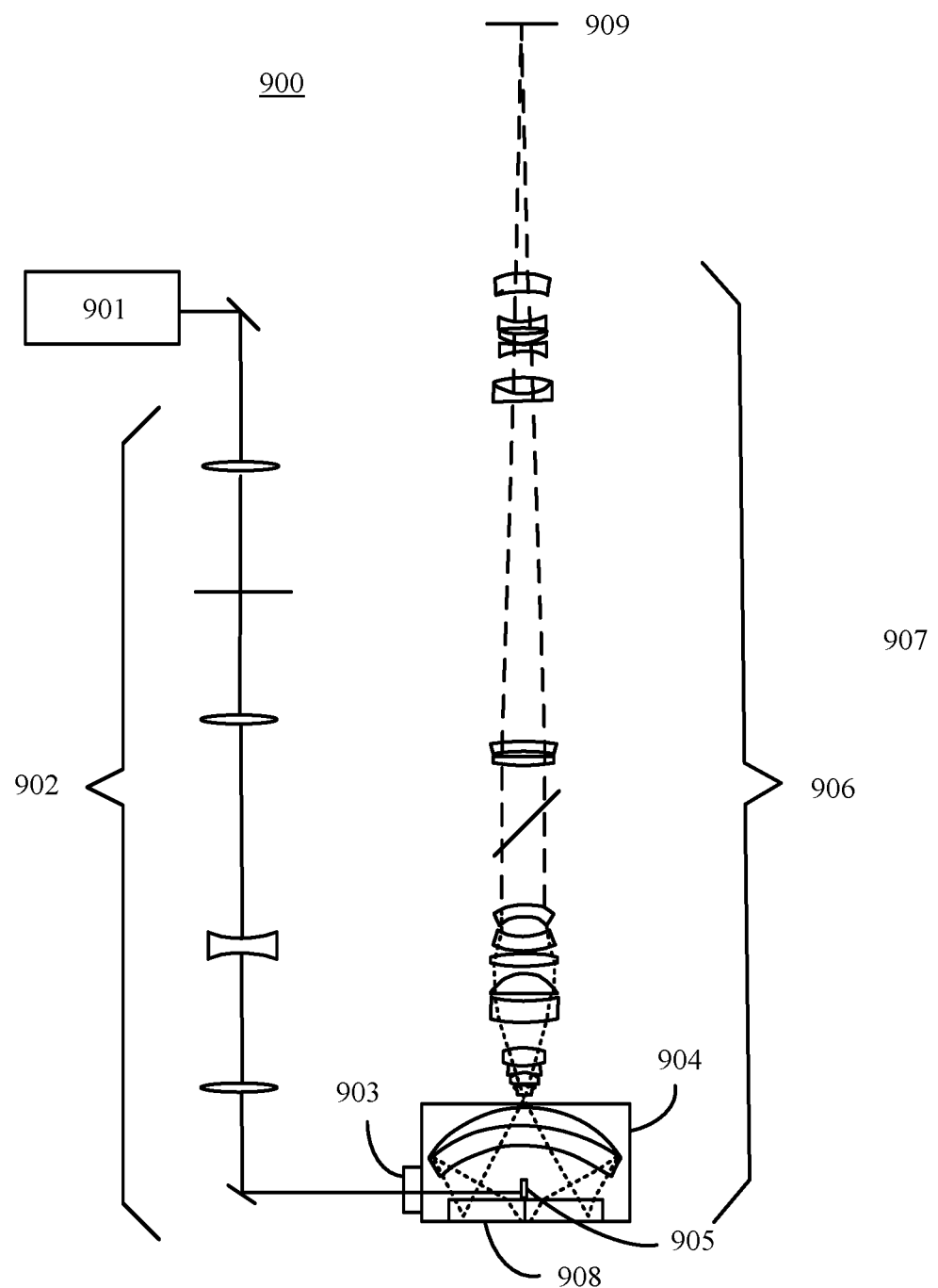

FIG. 9 illustrates the addition of a normal incidence laser illumination (dark-field or bright-field) to a catadioptric imaging system 900. The illumination block of system 900 includes a laser 901, adaptation optics 902 to control the illumination beam size and profile on the surface being inspected, an aperture and window 903 in a mechanical housing 904, and a prism 905 to redirect the laser along the optical axis at normal incidence to the surface of a sample 908. Prism 905 also directs the specular reflection from surface features of sample 908 and reflections from the optical surfaces of an objective 906 along the optical path to an image plane 909. Lenses for objective 906 can be provided in the general form of a catadioptric objective, a focusing lens group, and a zooming tube lens section (see, e.g. FIG. 8). In a preferred embodiment, laser 901 can be implemented by one of the above-described improved DUV CW lasers. Published Patent Application 2007/0002465, which published on Jan. 4, 2007 and is incorporated by reference herein, describes system 900 in further detail.

Figure 10A:
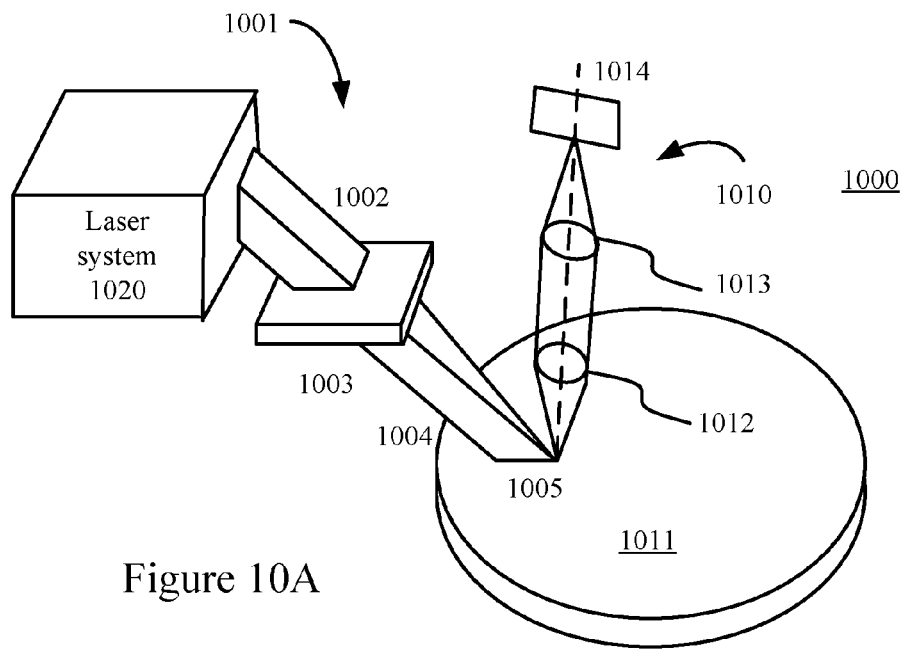

FIG. 10A illustrates a surface inspection apparatus 1000 that includes illumination system 1001 and collection system 1010 for inspecting areas of surface 1011. As shown in FIG. 10A, a laser system 1020 directs a light beam 1002 through a lens 1003. In a preferred embodiment, laser system 1020 includes one of the above-described improved DUV CW lasers. First beam shaping optics can be configured to receive a beam from the laser and focus the beam to an elliptical cross section at a beam waist in or proximate to the crystal.

Lens 1003 is oriented so that its principal plane is substantially parallel to a sample surface 1011 and, as a result, illumination line 1005 is formed on surface 1011 in the focal plane of lens 1003. In addition, light beam 1002 and focused beam 1004 are directed at a non-orthogonal angle of incidence to surface 1011. In particular, light beam 1002 and focused beam 1004 may be directed at an angle between about 1 degree and about 85 degrees from a normal direction to surface 1011. In this manner, illumination line 1005 is substantially in the plane of incidence of focused beam 1004.

Collection system 1010 includes lens 1012 for collecting light scattered from illumination line 1005 and lens 1013 for focusing the light coming out of lens 1012 onto a device, such as charge coupled device (CCD) 1014, comprising an array of light sensitive detectors. In one embodiment, CCD 1014 may include a linear array of detectors. In such cases, the linear array of detectors within CCD 1014 can be oriented parallel to illumination line 1015. In one embodiment, multiple collection systems can be included, wherein each of the collection systems includes similar components, but differ in orientation.

Figure 10B:
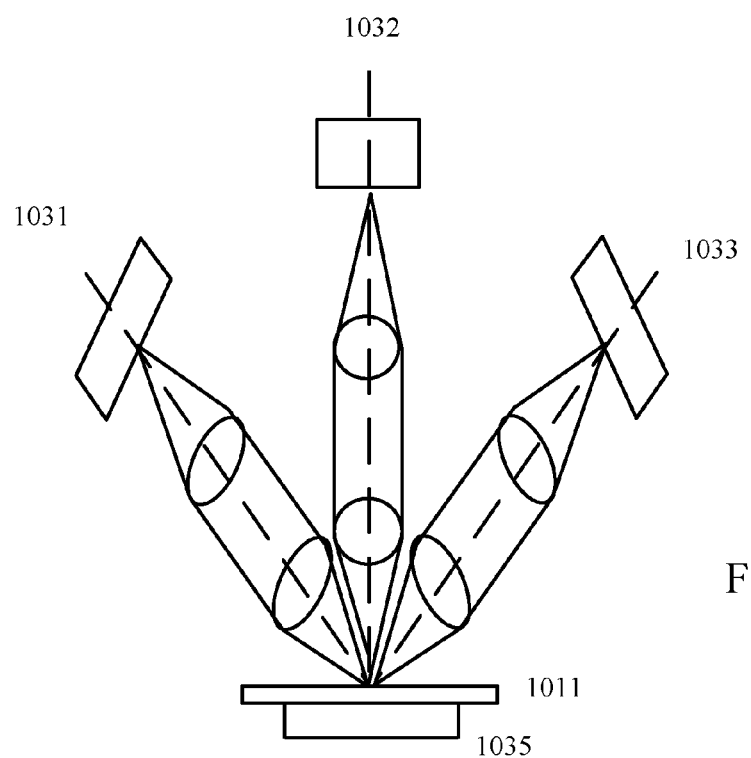

For example, FIG. 10B illustrates an exemplary array of collection systems 1031, 1032, and 1033 for a surface inspection apparatus (wherein its illumination system, e.g. similar to that of illumination system 1001, is not shown for simplicity). First optics in collection system 1031 collect light scattered in a first direction from the surface of sample 1011. Second optics in collection system 1032 collect light scattered in a second direction from the surface of sample 1011. Third optics in collection system 1033 collect light scattered in a third direction from the surface of sample 1011. Note that the first, second, and third paths are at different angles of reflection to said surface of sample 1011. A platform 1035 supporting sample 1011 can be used to cause relative motion between the optics and sample 1011 so that the whole surface of sample 1011 can be scanned. U.S. Pat. No. 7,525,649, which issued on Apr. 28, 2009 and is incorporated by reference herein, describes surface inspection apparatus 1000 and other multiple collection systems in further detail.

Figure 11:
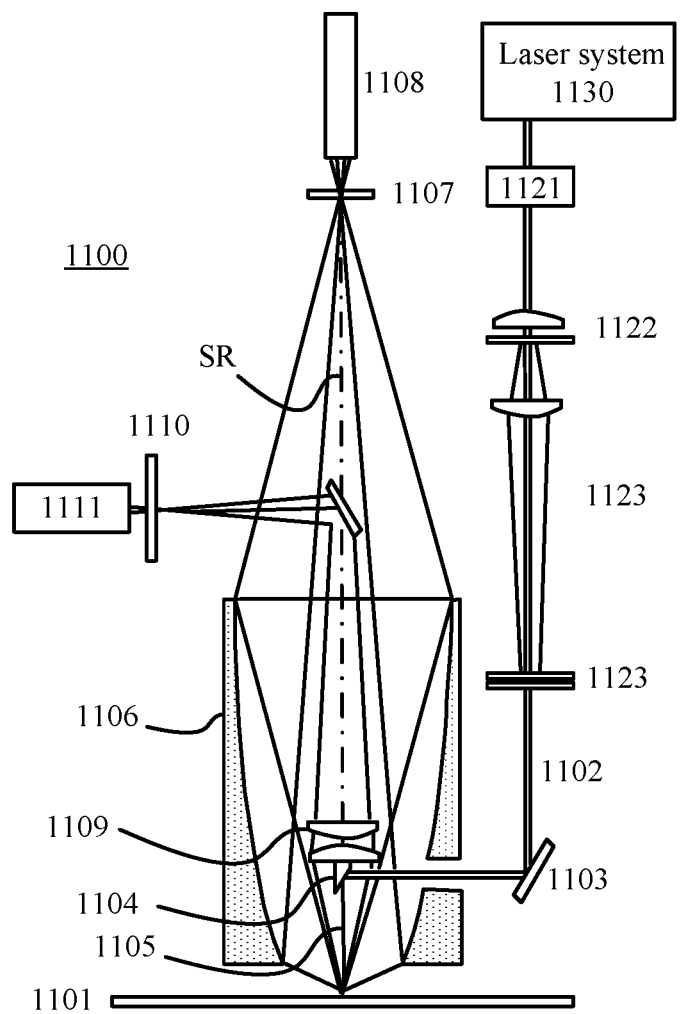

FIG. 11 illustrates a surface inspection system 1100 that can be used for inspecting anomalies on a surface 1101. In this embodiment, surface 1101 can be illuminated by a substantially stationary illumination device portion of a laser system 1130 comprising a laser beam generated by one of the above-described improved DUV CW lasers. The output of laser system 1130 can be consecutively passed through polarizing optics 1121, a beam expander and aperture 1122, and beam-forming optics 1123 to expand and focus the beam.

The resulting focused laser beam 1102 is then reflected by a beam folding component 1103 and a beam deflector 1104 to direct the beam 1105 towards surface 1101 for illuminating the surface. In the preferred embodiment, beam 1105 is substantially normal or perpendicular to surface 1101, although in other embodiments beam 1105 may be at an oblique angle to surface 1101.

In one embodiment, beam 1105 is substantially perpendicular or normal to surface 1101 and beam deflector 1104 reflects the specular reflection of the beam from surface 1101 towards beam turning component 1103, thereby acting as a shield to prevent the specular reflection from reaching the detectors. The direction of the specular reflection is along line SR, which is normal to the surface 1101 of the sample. In one embodiment where beam 1105 is normal to surface 1101, this line SR coincides with the direction of illuminating beam 1105, where this common reference line or direction is referred to herein as the axis of inspection system 1100. Where beam 1105 is at an oblique angle to surface 1101, the direction of specular reflection SR would not coincide with the incoming direction of beam 1105; in such instance, the line SR indicating the direction of the surface normal is referred to as the principal axis of the collection portion of inspection system 1100.

Light scattered by small particles is collected by mirror 1106 and directed towards aperture 1107 and detector 1108. Light scattered by large particles are collected by lenses 1109 and directed towards aperture 1110 and detector 1111. Note that some large particles will scatter light that is also collected and directed to detector 1108, and similarly some small particles will scatter light that is also collected and directed to detector 1111, but such light is of relatively low intensity compared to the intensity of scattered light the respective detector is designed to detect. In one embodiment, detector 1111 can include an array of light sensitive elements, wherein each light sensitive element of the array of light sensitive elements is configured to detect a corresponding portion of a magnified image of the illumination line. In one embodiment, inspection system can be configured for use in detecting defects on unpatterned wafers. U.S. Pat. No. 6,271,916, which issued on Aug. 7, 2001 and is incorporated by reference herein, describes inspection system 1100 in further detail.

Figure 12:
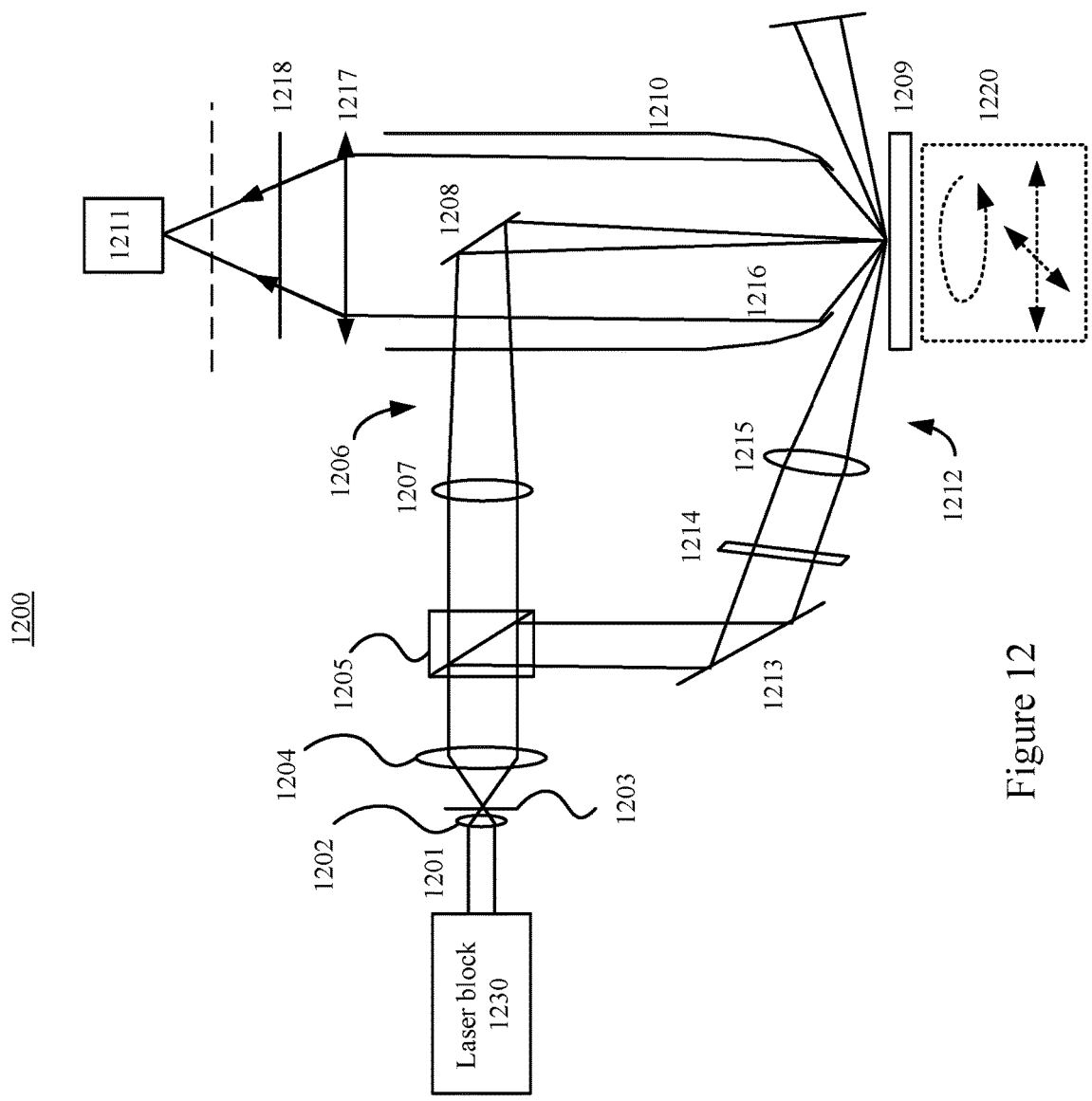

FIG. 12 illustrates an inspection system 1200 configured to implement anomaly detection using both normal and oblique illumination beams. In this configuration, a laser block 1230, which includes one of the above-described improved DUV CW lasers, can provide a laser beam 1201. A lens 1202 focuses the beam 1201 through a spatial filter 1203 and lens 1204 collimates the beam and conveys it to a polarizing beam splitter 1205. Beam splitter 1205 passes a first polarized component to the normal illumination channel and a second polarized component to the oblique illumination channel, where the first and second components are orthogonal. In the normal illumination channel 1206, the first polarized component is focused by optics 1207 and reflected by mirror 1208 towards a surface of a sample 1209. The radiation scattered by sample 1209 is collected and focused by a paraboloidal mirror 1210 to a photomultiplier tube 1211.

In the oblique illumination channel 1212, the second polarized component is reflected by beam splitter 1205 to a mirror 1213 which reflects such beam through a half-wave plate 1214 and focused by optics 1215 to sample 1209. Radiation originating from the oblique illumination beam in the oblique channel 1212 and scattered by sample 1209 is also collected by paraboloidal mirror 1210 and focused to photomultiplier tube 1211. Note that photomultiplier tube 1211 has a pinhole entrance. The pinhole and the illuminated spot (from the normal and oblique illumination channels on surface 1209) are preferably at the foci of the paraboloidal mirror 1210.

The paraboloidal mirror 1210 collimates the scattered radiation from sample 1209 into a collimated beam 1216. Collimated beam 1216 is then focused by an objective 1217 and through an analyzer 1218 to the photomultiplier tube 1211. Note that curved mirrored surfaces having shapes other than paraboloidal shapes may also be used. An instrument 1220 can provide relative motion between the beams and sample 1209 so that spots are scanned across the surface of sample 1209. U.S. Pat. No. 6,201,601, which issued on Mar. 13, 2001 and is incorporated by reference herein, describes inspection system 1200 in further detail.

Other reticle, photomask, or wafer inspection systems can advantageously use one of the above-described improved DUV CW lasers. For example, other systems include those described in the following U.S. Pat. Nos. 5,563,702, 5,999,310, 6,201,601, 6,271,916, 7,352,457, 7,525,649, and 7,528,943. Yet further systems include those described in US Publications 2007/0002465 and 2009/0180176. The patents, patent publications, and patent applications cited in this paragraph are incorporated by reference herein.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art. Accordingly, it is intended that the scope of the invention be defined by the following claims and their equivalents.

The invention claimed is:

1. A laser for generating deep ultra-violet (DUV) continuous wave (CW) light, the laser comprising:
   a second-harmonic generator configured to convert light having a fundamental wavelength to light having a second harmonic wavelength; and
   a fourth-harmonic generator configured to convert the light having the second harmonic wavelength to light having a fourth harmonic wavelength, the fourth-harmonic generator including:
   a plurality of mirrors configured to circulate light in the fourth harmonic generator;
   a first non-linear optical (NLO) crystal having first optical axes that are oriented relative to the light circulated in the fourth harmonic generator such that said first NLO crystal converts a portion of the light having the second harmonic wavelength to light having the fourth harmonic wavelength and having a first astigmatism, the first NLO crystal in operative relation to the plurality of mirrors; and
   a pair of thin plates, each said thin plate having parallel planar surfaces, said pair of thin plates disposed in operative relation to the first NLO crystal such that the light circulated in the fourth harmonic generator passes through said planar parallel surfaces of the pair of thin plates,
   wherein the pair of thin plates are disposed in a tilted arrangement at substantially equal and opposite angles about respective parallel axes such that the pair of thin plates introduce a second astigmatism to the light circulated in the fourth harmonic generator that corrects for said first astigmatism while minimizing displacement of said circulated light, and wherein the first NLO crystal comprises a hydrogen-annealed cesium lithium borate (CLBO) crystal.

2. A laser for generating deep ultra-violet (DW) continuous wave (CW) light, the laser comprising:
   a second-harmonic generator configured to convert light having a fundamental wavelength to light having a second harmonic wavelength; and
   a fourth-harmonic generator configured to convert the light having the second harmonic wavelength to light having a fourth harmonic wavelength, the fourth-harmonic generator including:
   a plurality of mirrors configured to circulate light in the fourth harmonic generator;
   a first non-linear optical (NLO) crystal having first optical axes that are oriented relative to the light circulated in the fourth harmonic generator such that said first NLO crystal converts a portion of the light having the second harmonic wavelength to light having the fourth harmonic wavelength and having a first astigmatism, the first NLO crystal in operative relation to the plurality of mirrors; and
   a pair of thin plates, each said thin plate having parallel planar surfaces, said pair of thin plates disposed in operative relation to the first NLO crystal such that the light circulated in the fourth harmonic generator passes through said planar parallel surfaces of the pair of thin plates,
   wherein the pair of thin plates are disposed in a tilted arrangement at substantially equal and opposite angles about respective parallel axes such that the pair of thin plates introduce a second astigmatism to the light circulated in the fourth harmonic generator that corrects for said first astigmatism while minimizing displacement of said circulated light, and
   wherein said plurality of mirrors configured to circulate light in the fourth harmonic generator include a spherical mirror configured such that the light having the second harmonic is focused to a substantially elliptical beam waist in, or proximate to, the first NLO crystal, with a long axis of an ellipse substantially parallel to a first e-axis.

3. The laser of claim 1, further comprising means for maintaining a temperature of at least the first NLO crystal below 100° C. to minimize said first astigmatism created in the first NLO crystal.

4. The laser of claim 3, wherein said means is configured to maintain said temperature is approximately 50° C. or lower.

5. The laser of claim 1, wherein the fourth harmonic generator further comprises a feedback control loop that automatically adjusts the substantially equal and opposite angles of the pair of thin plates so as to substantially cancel said first astigmatism introduced by the first NLO crystal.

6. A system for inspecting a wafer, reticle, or photomask, the system comprising:
   a deep ultra-violet (DUV) continuous wave (CW) laser including:
   a second harmonic generator for converting light having a fundamental wavelength to light having a second harmonic wavelength; and
   a fourth harmonic generator for converting the light having the second harmonic wavelength to light having a fourth harmonic wavelength, the fourth harmonic generator including:
   a plurality of mirrors configured to circulate light in the fourth harmonic generator;
   a first non-linear optical (NLO) crystal configured to generate the light having the fourth harmonic wavelength by converting a converted portion of the light having the second harmonic wavelength, the first NLO crystal in operative relation to the plurality of mirrors such that the light circulating in the fourth harmonic generator is directed into the first NLO crystal only in a single light propagation direction; and
   a pair of thin plates, each said thin plate having parallel planar surfaces, said pair of thin plates disposed in operative relation to the first NLO crystal such that the light circulated in the fourth harmonic generator passes through said planar parallel surfaces of the pair of thin plates,
   wherein the pair of thin plates are disposed in a tilted arrangement at substantially equal and opposite angles about respective parallel axes such that the pair of thin plates introduce a second astigmatism to the light circulated in the fourth harmonic generator that corrects for said first astigmatism while minimizing displacement of said circulated light, and
   wherein the first NLO crystal comprises a hydrogen-annealed CLBO (cesium lithium borate) crystal.

7. The system of claim 6, wherein said plurality of mirrors configured to circulate light in the fourth harmonic generator include a spherical mirror configured such that light having the second harmonic is focused to a substantially elliptical beam waist in, or proximate to, the first NLO crystal, with a long axis of an ellipse substantially parallel to a first e-axis.

8. The system of claim 6, further comprising means for maintaining a temperature of at least the first NLO crystal below 100° C. to minimize said first astigmatism created in the first NLO crystal.

9. The system of claim 8, wherein said means is configured to maintain said temperature is approximately 50° C. or lower.

10. The system of claim 6, wherein the fourth harmonic generator further comprises a feedback control loop that automatically adjusts the substantially equal and opposite angles of the pair of thin plates so as to substantially cancel said first astigmatism introduced by the first NLO crystal.

11. A method of generating deep ultra-violet (DUV) continuous wave (CW) light in a laser, the method including:
   converting light having a fundamental wavelength to light having a second harmonic wavelength;
   converting a portion of the light having the second harmonic wavelength to light having a fourth harmonic wavelength by circulating the light having the second harmonic wavelength in a cavity configured such that said light passes through a hydrogen-annealed cesium lithium borate (CLBO) crystal only in a single light propagation direction; and
   cancelling a first astigmatism created in the hydrogen-annealed CLBO crystal using a pair of thin plates, each said thin plate having parallel planar surfaces, said pair of thin plates disposed in operative relation to the hydrogen-annealed CLBO crystal such that the light circulated in the fourth harmonic generator passes through said planar parallel surfaces of the pair of thin plates,
   wherein the pair of thin plates are disposed in a tilted arrangement at substantially equal and opposite angles about respective parallel axes such that the pair of thin plates introduce a second astigmatism to the light circulated in the fourth harmonic generator that corrects for said first astigmatism while minimizing displacement of said circulated light.

\* \* \* \* \*